(12) United States Patent
Wu

(10) Patent No.: US 9,234,213 B2
(45) Date of Patent: *Jan. 12, 2016

(54) COMPOSITIONS AND METHODS DIRECTED TO CRISPR/CAS GENOMIC ENGINEERING SYSTEMS

(71) Applicant: System Biosciences, LLC, Mountain View, CA (US)

(72) Inventor: Fangting Wu, Mountain View, CA (US)

(73) Assignee: System Biosciences, LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/211,858

(22) Filed: Mar. 14, 2014

(65) Prior Publication Data

US 2014/0273037 A1     Sep. 18, 2014

Related U.S. Application Data

(60) Provisional application No. 61/799,586, filed on Mar. 15, 2013.

(51) Int. Cl.
| C12N 15/90 | (2006.01) |
| C12N 9/22 | (2006.01) |
| C12N 15/85 | (2006.01) |
| C12N 15/10 | (2006.01) |

(52) U.S. Cl.
CPC ............... *C12N 15/907* (2013.01); *C12N 9/22* (2013.01); *C12N 15/102* (2013.01); *C12N 15/85* (2013.01)

(58) Field of Classification Search
None
See application file for complete search history.

(56) References Cited

U.S. PATENT DOCUMENTS

| 5,571,690 | A * | 11/1996 | Hecht ........................... 435/69.1 |
| 8,252,535 | B2 | 8/2012 | Biekle et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 2010/0076057 | A1 | 3/2010 | Sontheimer et al. |
| 2010/0093617 | A1 | 4/2010 | Barrangou et al. |
| 2010/0104690 | A1 | 4/2010 | Barrangou et al. |
| 2011/0002889 | A1 | 1/2011 | Barrangou et al. |
| 2011/0189776 | A1 | 8/2011 | Terns et al. |
| 2011/0300538 | A1 | 12/2011 | Barrangou et al. |
| 2013/0011828 | A1 | 1/2013 | Barrangou et al. |
| 2014/0068797 | A1* | 3/2014 | Doudna et al. ................ 800/18 |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |
| 2014/0242664 | A1 | 8/2014 | Zhang et al. |
| 2014/0242699 | A1 | 8/2014 | Zhang |
| 2014/0248702 | A1 | 9/2014 | Cong et al. |
| 2014/0256046 | A1 | 9/2014 | Zhang et al. |
| 2014/0310830 | A1 | 10/2014 | Zhang et al. |
| 2014/0342456 | A1 | 11/2014 | Mali et al. |
| 2014/0342457 | A1 | 11/2014 | Mali et al. |
| 2014/0342458 | A1 | 11/2014 | Mali et al. |
| 2014/0356956 | A1 | 12/2014 | Church et al. |
| 2014/0356958 | A1 | 12/2014 | Mali et al. |
| 2014/0356959 | A1 | 12/2014 | Church et al. |
| 2014/0357530 | A1 | 12/2014 | Zhang et al. |
| 2015/0020223 | A1 | 1/2015 | Zhang et al. |

FOREIGN PATENT DOCUMENTS

| WO | 2006/055836 | 5/2006 |
| WO | 2007/025097 | 3/2007 |
| WO | 2008/052101 | 5/2008 |
| WO | 2008/122314 | 10/2008 |
| WO | 2010/011961 | 1/2010 |
| WO | 2010/054154 | 5/2010 |
| WO | 2010/075424 | 7/2010 |
| WO | 2012/054726 | 4/2012 |
| WO | 2012/164565 | 12/2012 |
| WO | 2013/176772 | 11/2013 |
| WO | 2014/093595 | 6/2014 |
| WO | 2014/093622 | 6/2014 |

(Continued)

OTHER PUBLICATIONS

Cong et al. (2013) Multiplex Genome Engineering Using CRISPR/Cas Systems. Science, 339:819-822, and supplementary materials.*
Fath et al. (2011) Multiparameter RNA and Codon Optimization: A Standardized Tool to Assess and Enhance Autologous Mammalian Gene Expression. PLoS ONE, 6(3):e17596, pp. 1-14.*
Barrangou, "RNA-mediated programmable DNA cleavage." Nature Biotechnology, 30(9), p. 836-838 (Sep. 2012).
Bassett et al., "Highly Efficient Targeted Mutagenesis of *Drosophila* with the CRISPR/Cas9 System," Cell Rep., 4 (1):220-228 (Jul. 11, 2013).

(Continued)

*Primary Examiner* — Michele K Joike
*Assistant Examiner* — Neil P Hammell
(74) *Attorney, Agent, or Firm* — Dergosits & Noah LLP

(57) ABSTRACT

The invention relates to engineered CRISPR/Cas9 systems for genomic modification in mammalian cells. The present specification describes the design and testing of a polynucleotide encoding the *Streptococcus pyogenes* (*S. pyogenes*) Cas9 protein, where the nucleotide sequence has been optimized for expression in mammalian cells. The specification also describes all-in-one systems for RNA-guided genome engineering in mammalian cells, including human cells.

7 Claims, 26 Drawing Sheets

(56) References Cited

FOREIGN PATENT DOCUMENTS

| WO | 2014/093635 | 6/2014 |
|---|---|---|
| WO | 2014/093655 | 6/2014 |
| WO | 2014/093661 | 6/2014 |
| WO | 2014/093694 | 6/2014 |
| WO | 2014/093701 | 6/2014 |
| WO | 2014/093709 | 6/2014 |
| WO | 2014/093712 | 6/2014 |
| WO | 2014/093718 | 6/2014 |
| WO | 2014/099744 | 6/2014 |
| WO | 2014/099750 | 6/2014 |
| WO | 2014/197568 | 12/2014 |

OTHER PUBLICATIONS

Bhaya et al., "CRISPR-Cas systems in bacteria and archaea: versatile small RNAs for adaptive defense and regulation," Annu. Rev. Genet. 45, 273 (2011).

Brouns, "A Swiss Army Knife of Immunity" Science 337: p. 808-809 (Aug. 17, 2012).

Burgess, "A CRISPR genome-editing tool." Nature Reviews—Genetics vol. 14 (Feb. 2013), published online Jan. 16, 2013.

Carr and Church, "Genome engineering," Nat. Biotechnol. 27, 1151 (2009).

Cho et al., "Targeted genome engineering in human cells with the Cas9 RNA-guided endonuclease," Nature Biotechnology 31:230-232 (epub Jan. 29, 2013).

Cong et al., "Multiplex Genome Engineering Using CRISPR/Cas Systems" Science 339(6121):819-823 (Feb. 15, 2013), epub Science Express (Jan. 3, 2013).

Gilbert et al., "CRISPR-mediated modular RNA-guided regulation of transcription in eukaryotes," Cell 154(2):442-451 (epub Jul. 11, 2013).

Hale et al., "Essential Features and Rational Design of CRISPR RNAs that Function with the Cas RAMP Module Complex to Cleave RNAs." Molecular Cell 45, p. 292-302 (print Feb. 10, 2012) [epub: Jan. 5, 2012].

Hwang et al. "Efficient genome editing in zebrafish using a CRISPR-Cas system." Nat. Biotechnol. advance online publication (Jan. 29, 2013).

Jiang et al, "RNA-guided editing of bacterial genomes using CRISPR-Cas systems," Nature Biotechnol., 31(3):233-239 (Mar. 2013; epub Jan. 29, 2013).

Jinek et al., (2012) "A Programmable Dual-RNA—Guided DNA Endonuclease in Adaptive Bacterial Immunity" Science 337(6096): p. 816-821 (print edition Aug. 17, 2012; epub Science Express, Jun. 28, 2012).

Jinek et al., RNA-programmed genome editing in human cells. (Jan. 29, 2013) eLife 2:e00471.

Koike-Yusa et al., "Genome-wide recessive genetic screening in mammalian cells with a lentiviral CRISPR-guide RNA library," Nature Biotechnology 32:267-273 (2014); epub Dec. 23, 2013.

Konermann et al., "Optical control of mammalian endogenous transcription and epigenetic states," Nature 500 (7463):472-476 (2013); epub Jul. 23, 2013.

Mäkinen et al., "Stable RNA interference: comparison of U6 and H1 promoters in endothelial cells and in mouse brain" J Gene Med. 8(4):433-441 (2006).

Mali et al., "RNA-Guided Human Genome Engineering via Cas9" Science 339(6121):823-826 (Feb. 15, 2013), epub Science Express (Jan. 3, 2013).

Mali et al., "CAS9 transcriptional activators for target specificity screening and paired nickases for cooperative genome engineering," Nature Biotechnology 31:833-838 (epub Aug. 1, 2013).

Makarova et al., "Evolution and classification of the CRISPR-Cas systems." Nat. Rev. Microbiol. 9, 467 (2011).

Perez-Pinera et al, "RNA-guided gene activation by CRISPR-Cas9-based transcription factors," Nature Methods 10:973-976 (epub Jul. 25, 2013).

Ran et al., "Double Nicking by RNA-Guided CRISPR Cas9 for Enhanced Genome Editing Specificity." Cell 154 (6):1380-1389 (Sep. 2013).

Segal, "Bacteria herald a new era of gene editing," eLife, Jan. 29, 2013; 2:e00563.

Shalem et al, "Genome-Scale CRISPR-Cas9 Knockout Screening in Human Cells," Science (Jan. 3, 2014) p. 84-87, epub Sciencexpress Dec. 12, 2013.

Shen et al., "Generation of gene-modified mice via Cas9/RNA-mediated gene targeting," Cell Res., 23(5):720-723 (May 2013; epub Apr. 2, 2013).

Sontheimer and Marraffini, "Slicer for DNA" Nature 468:p. 45-46 (in print Nov. 4, 2010; epub Nov. 3, 2010).

Sorek et al., "CRISPR—a widespread system that provides acquired resistance against phages in bacteria and archaea," Nature Reviews Microbiology 6:181-186 (Mar. 2008).

System Biosciences, Inc., pGreenFire™ Pathway Reporter Lentivectors Cat. # TR0XX Series User Manual, 19 pgs, dated Aug. 24, 2012.

System Biosciences, Inc., "PrecisionX Cas9 SmartNuclease™ Vector System, Catalog Nos. CASxxx series User Manual," ver.1, dated Apr. 22, 2013 (16 pages), retrieved from <http://www.systembio.com/downloads/Cas9-SmartNuclease-user-manual.pdf>.

System Biosciences, Inc., "PrecisionX Cas9 SmartNuclease™ RNA System, Catalog Nos. CAS5xxA-1 series User Manual," ver.2, dated Sep. 3, 2013 17 pages, retrieved from <http://www.systembio.com/downloads/CAS5xxA-1-gRNA_Cas9_mRNA.pdf>.

Terns and Terns, "CRISPR-based adaptive immune systems." Curr. Opin. Microbiol. 14, 321 (2011).

Wang et al., "One-step generation of mice carrying mutations in multiple genes by CRISPR/Cas-mediated genome engineering," Cell 153(4):910-918 (May 9, 2013; epub May 2, 2013).

Wiedenheft, Sternberg and Doudna, "RNA-guided genetic silencing systems in bacteria and archaea." Nature 482; p. 331-338 (print Feb. 15, 2012; epub Feb. 15, 2012).

Sanders "Cheap and easy technique to snip DNA could revolutionize gene therapy." Media Relations, Univ. of California Berkeley, NewsCenter website (dated Jan. 7, 2013). Retrieved from: <URL: http://newscenter.berkeley.edu/2013/01/07/cheap-and-easy-technique-to-snip-dna-could-revolutionize-gene-therapy/>.

Cain, "CRISPR genome editing," SciBX Science-Business eXchange 6(4); doi: 10.1038/scibx.2013.77 (epub Jan. 31, 2013).

Collins, "Copy-editing the Genome: Extreme Personalized Medicine?" NIH Director's Blog (Jan. 22, 2013); retrieved from: <URL: http://directorsblog.nih.gov/copy-editing-the-genome-extreme-personalized-medicine/>; [retrieved on xx/xx/xx].

Leuty "QB3 powers new wave of bio startups," San Francisco Business Times (dated Sep. 14, 2012); retrieved from: <http://www.bizjournals.com/sanfrancisco/print-edition/2012/09/14/qb3-powers-new-wave-of-bio-startups.html?page=all>; [retrieved approximately Feb. 2013].

Addgene, "CRISPR/Cas Plasmids and Protocols," webpage retrieved from: <https://www.addgene.org/CRISPR/>; [retrieved on May 8, 2014].

Addgene, "CRISPR/Cas Plasmids for use in: Mammals," webpage retrieved from: <https://www.addgene.org/CRISPR/mammalian/>; [retrieved on May 8, 2014].

National Center for Biotechnology Information (NCBI), National Institutes of Health, Gen Bank® Accession No. AAK33936.1, Apr. 1, 2014.

National Center for Biotechnology Information (NCBI), National Institutes of Health, GenBank® Accession No. NC_002737, Jun. 27, 2013.

Sapranauskas et al. Nucleic Acids Research, 2011, 1-8, complete citation: Sapranauskas et al. (2011) Nucleic Acids Research, 39 (21) :9275-9272.

Office Action, United States Patent and Trademark Office <www.uspto.gov>, U.S. Appl. No. 14/216,655 (now published US2014/0273226), communication mailing date Aug. 4, 2015.

\* cited by examiner

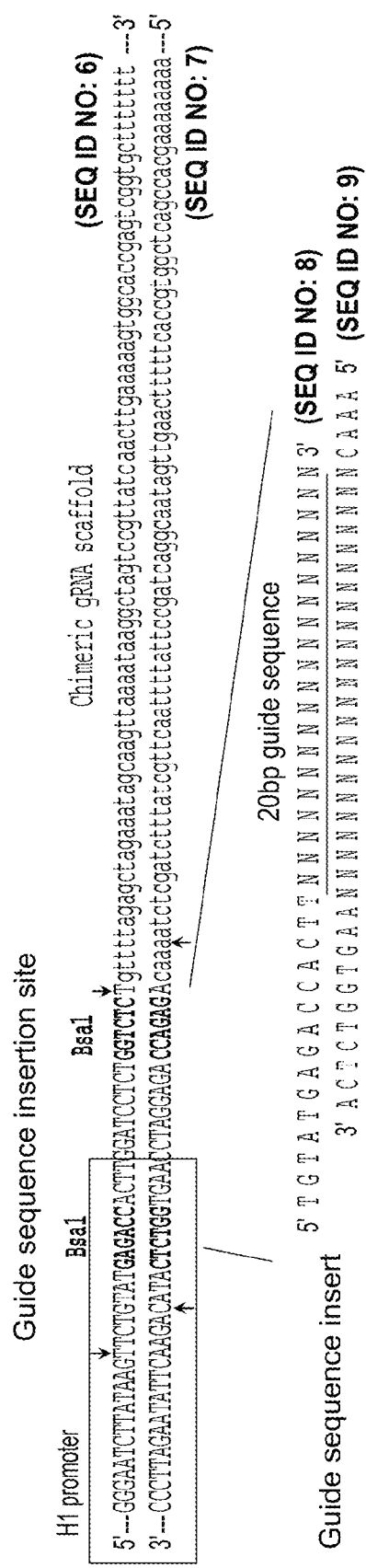
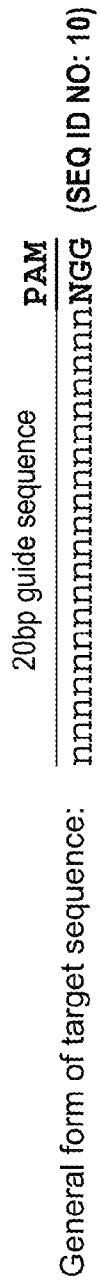
FIG. 1B
FIG. 1C

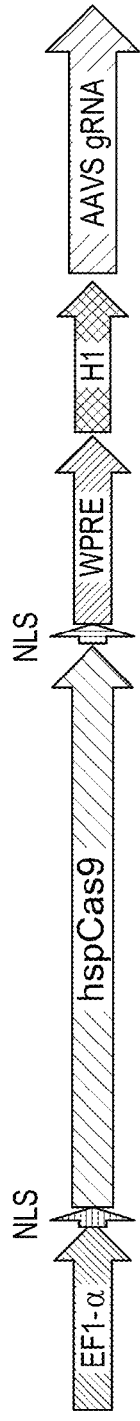
FIG. 3A
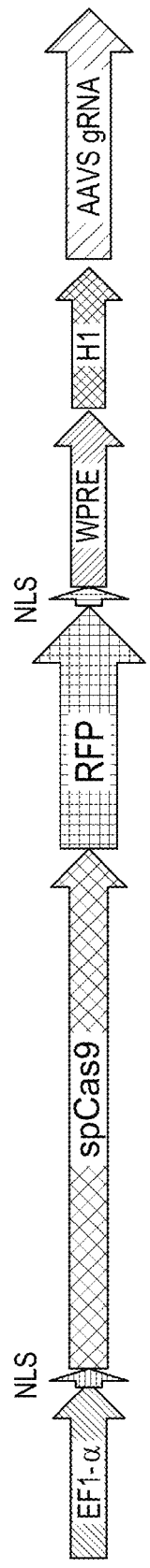
FIG. 3B
AAVS target sequence: GGGGCCACTAGGGACAGGAT (SEQ ID NO: 11)
FIG. 3C

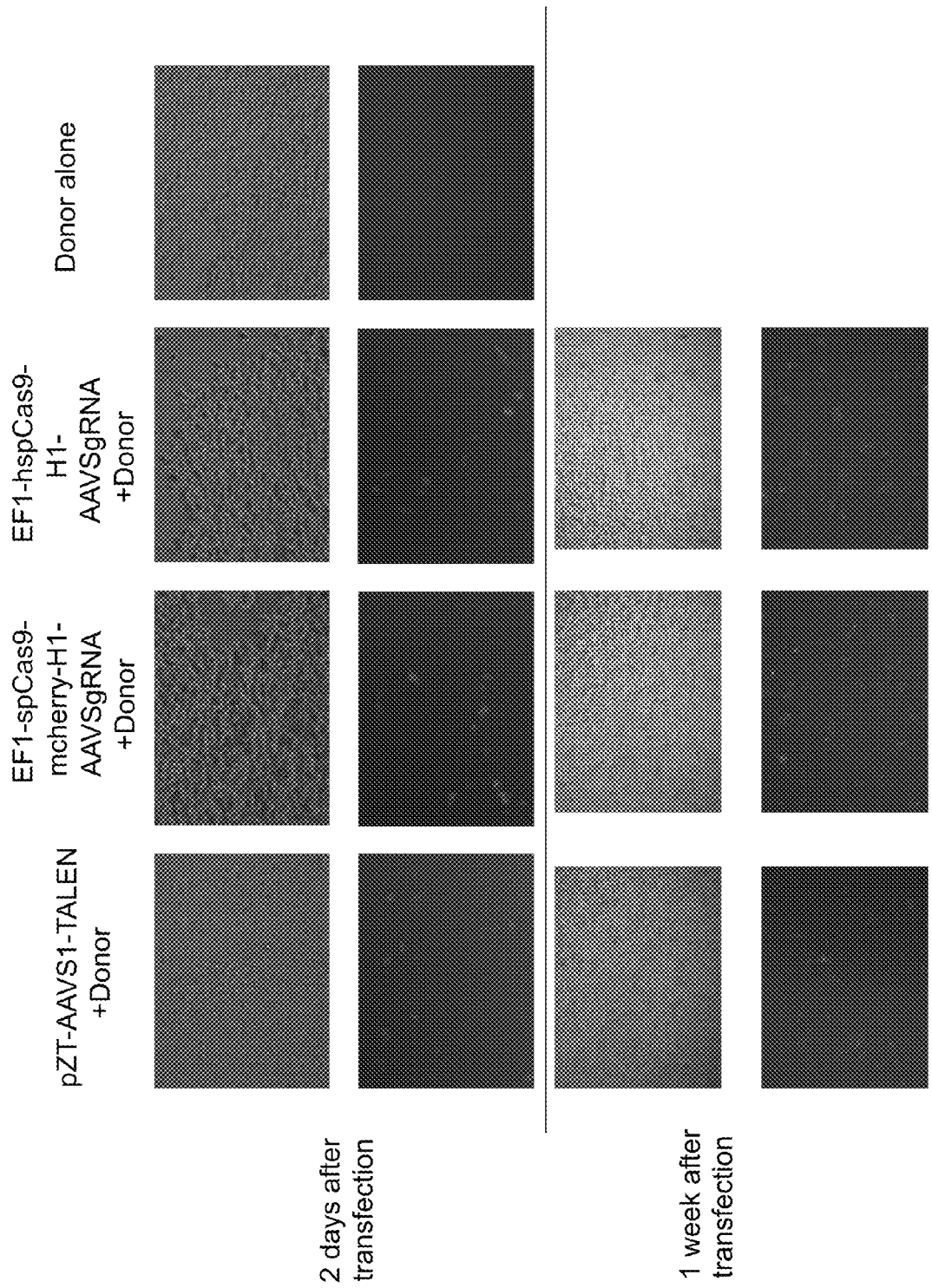

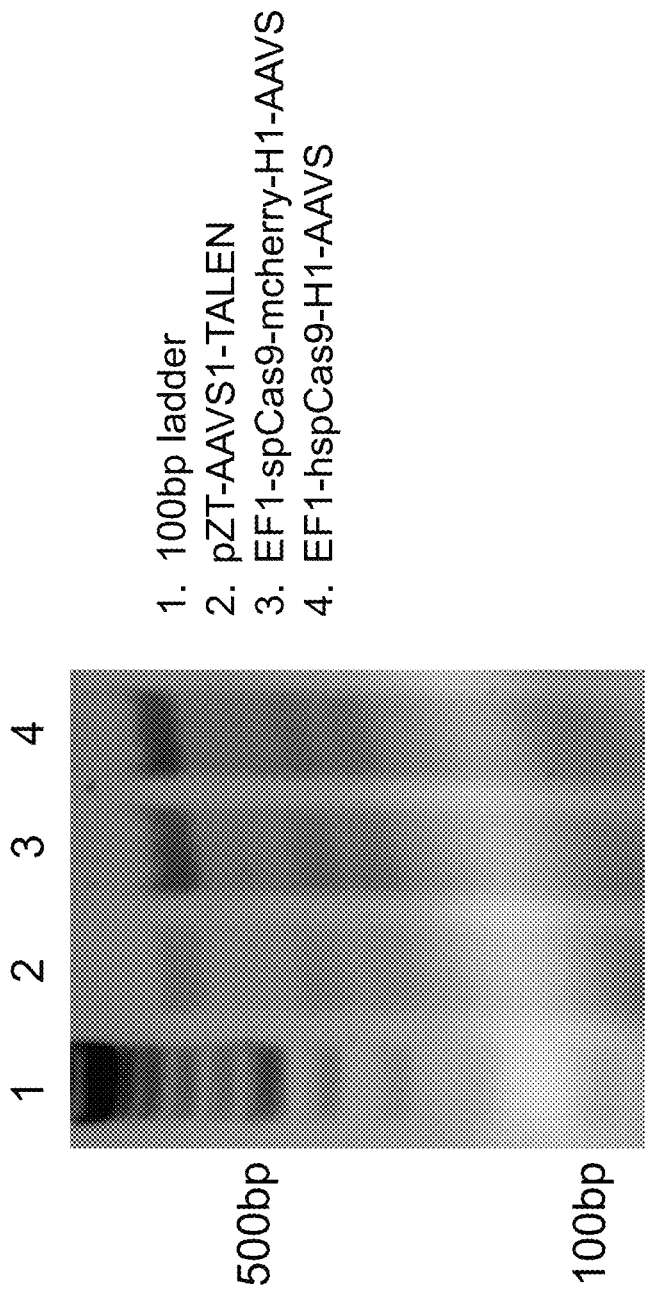

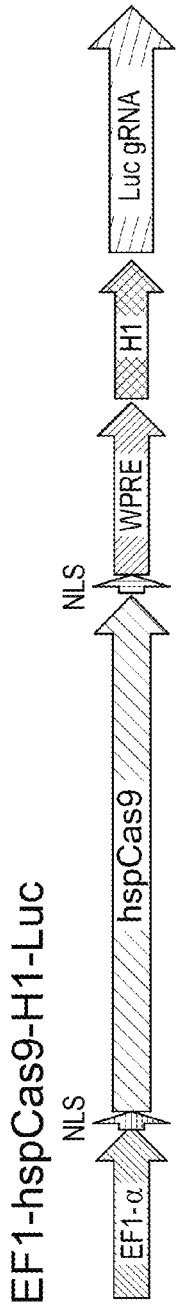
FIG. 6A
Luciferase gRNA sequences:
Luc gRNA1: GGCATGGCGAGAATCTGACGC (SEQ ID NO: 13)
Luc gRNA2: CATGCCAGAGATCCTATTT (SEQ ID NO: 14)
FIG. 6B
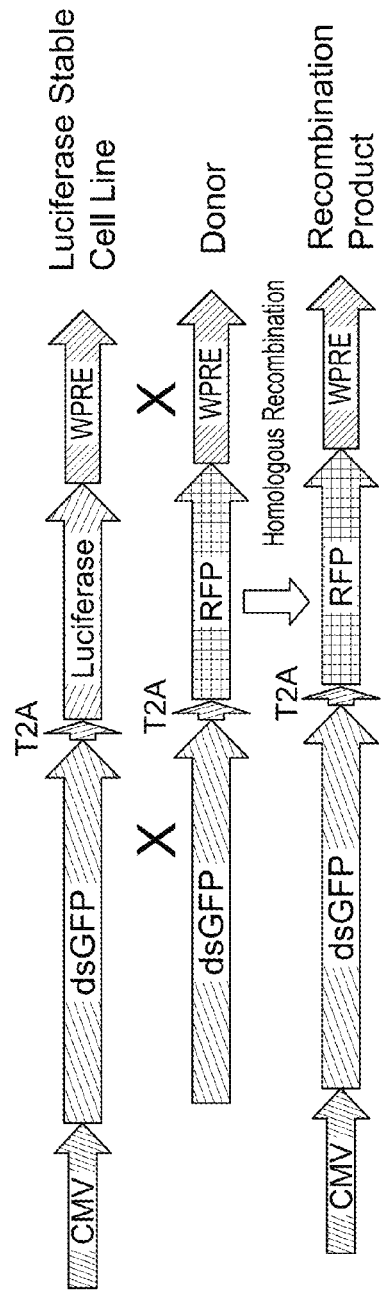
FIG. 6C atggctagtatgcagaaactgattagtgaagaggacctgATGGCTCCCAAGAAGAAGCGAAAGG
TGGGCATCCACGGCGTGCCCGCTGCCGACAAAAAGTATAGTATCGGACTGGATATTGGCACTAA
CAGCGTGGGATGGGCCGTCATCACCGACGAGTACAAAGTGCCAAGCAAGAAGTTCAAGGTCCTG
GGAAACACCGATAGACACAGTATCAAGAAAAATCTGATTGGAGCCCTGCTGTTCGACTCAGGGG
AGACAGCTGAAGCAACTAGGCTGAAAAGAACAGCTAGGAGACGGTATACTCGCCGAAAGAATCG
GATCTGCTACCTCCAGGAGATTTTCTCCAACGAAATGGCCAAGGTGGACGATAGTTTCTTTCAT
CGCCTGGAGGAATCATTCCTGGTCGAGGAAGATAAGAAACACGAGAGGCATCCCATCTTTGGCA
ACATTGTGGACGAGGTCGCTTATCACGAAAGTACCCTACAATCTATCATCTGCGGAAGAAACT
GGTGGACAGCACTGATAAGGCAGACCTGCGCCTGATCTATCTGGCCCTGGCTCACATGATTAAG
TTCAGGGGGCATTTTCTGATCGAGGGCGATCTGAACCCAGACAATTCCGATGTGGACAAGCTGT
TCATCCAGCTGGTCCAGACATACAATCAGCTGTTTGAGGAAAACCCCATTAATGCATCTGGGGT
GGACGCAAAAGCCATCCTGAGTGCCAGACTGTCTAAGAGTAGGAGACTGGAGAACCTGATCGCT
CAGCTGCCAGGCGAAAAGAAAAACGGCCTGTTTGGAAATCTGATTGCACTGTCACTGGGACTGA
CCCCCAACTTCAAGAGCAATTTTGATCTGGCCGAGGACGCTAAGCTCCAGCTGAGCAAGGACAC
CTACGACGATGACCTGGATAACCTGCTGGCTCAGATCGGCGATCAGTACGCAGACCTGTTCCTG
GCCGCTAAGAATCTGTCTGACGCCATCCTGCTGAGTGATATTCTGAGAGTGAACACCGAGATTA
CAAAAGCCCCCCTGTCAGCTAGCATGATCAAGAGATATGACGAGCACCATCAGGATCTGACCCT
GCTGAAGGCTCTGGTGCGGCAGCAGCTGCCTGAGAAGTACAAAGAAATCTTCTTTGATCAGAGC
AAGAATGGGTACGCCGGCTATATTGACGGCGGAGCTTCCCAGGAGGAGTTCTACAAGTTTATCA
AACCTATTCTGGAGAAGATGGACGGCACTGAGGAACTGCTGGTGAAACTGAATCGGGAAGACCT
GCTGCGGAAGCAGCGCACCTTCGATAACGGCAGCATCCCTCACCAGATTCATCTGGGAGAGCTG
CACGCAATCCTGCGGCGCCAGGAAGACTTCTACCCATTTCTGAAGGATAACCGGGAGAAGATCG
AAAAAATTCTGACTTTCCGCATCCCCTACTATGTGGGCCTCTGGCAAGAGGCAATTCCCGGTT
TGCCTGGATGACCCGCAAGTCTGAGGAAACAATCACTCCCTGGAACTTCGAGGAAGTGGTCGAT
AAGGGCGCTTCCGCACAGTCTTTCATTGAGAGGATGACAAATTTTGACAAGAACCTGCCAAATG
AAAAAGTGCTGCCCAAGCACAGCCTGCTGTACGAGTATTTCACCGTCTATAACGAACTGACAAA FIG. 10 (part 1 of 3, continued next page)

GGTGAAATACGTCACTGAGGGCATGAGAAAGCCTGCCTTCCTGTCCGGAGAACAGAAGAAAGCT
ATCGTGGACCTGCTGTTTAAAACCAATCGGAAGGTGACAGTCAAGCAGCTGAAAGAGGACTACT
TCAAGAAAATTGAATGTTTCGATTCTGTGGAGATCAGTGGGGTCGAAGACAGGTTTAACGCCTC
TCTGGGCACCTACCACGATCTGCTGAAGATCATTAAGGATAAAGACTTCCTGGACAACGAGGAA
AATGAGGACATCCTGGAGGACATTGTGCTGACCCTGACACTGTTTGAGGATCGGGAAATGATCG
AGGAACGCCTGAAGACCTACGCCCATCTGTTCGATGACAAAGTGATGAAACAGCTGAAGCGAAG
GAGATACACTGGGTGGGGCCGACTGAGCAGGAAGCTGATCAATGGCATTCGCGACAAACAGAGT
GGAAAGACAATCCTGGACTTTCTGAAGTCAGATGGCTTCGCTAACAGGAATTTTATGCAGCTGA
TTCACGATGACTCTCTGACTTTCAAAGAGGACATCCAGAAGGCACAGGTGTCCGGACAGGGGGA
CTCTCTGCACGAGCATATCGCAAACCTGGCCGGGAGCCCTGCCATCAAGAAAGGCATCCTCCAG
ACCGTGAAGGTGGTGGACGAGCTGGTGAAAGTCATGGGAAGACATAAGCCAGAAAACATCGTGA
TTGAGATGGCCAGGGAGAATCAGACCACACAGAAAGGGCAGAAGAACTCTCGGGAGCGCATGAA
ACGCATCGAGGAAGGAATTAAGGAACTGGGGAGTCAGATCCTGAAAGAGCACCCCGTGGAAAAC
ACACAGCTCCAGAATGAGAAGCTGTATCTGTACTACCTCCAGAATGGCCGCGATATGTACGTGG
ACCAGGAGCTGGATATTAACCGACTGTCAGATTATGACGTGGATCATATCGTCCCACAGTCATT
CCTGAAAGATGACAGCATTGACAATAAGGTGCTGACCCGCAGCGACAAAAACCGAGGAAAGAGT
GATAATGTCCCCTCAGAGGAAGTGGTCAAGAAAATGAAGAACTACTGGAGGCAGCTGCTGAATG
CCAAACTGATCACCCAGCGAAAGTTTGATAACCTGACAAAAGCTGAGAGGGGGGGCCTGTCCGA
ACTGGACAAAGCAGGCTTCATCAAGCGACAGCTGGTGGAGACaAGGCAGATCACAAAGCACGTC
GCTCAGATCCTGGACAGCAGGATGAACACCAAGTACGATGAGAATGACAAACTGATCCGGGAAG
TGAAGGTCATTACACTGAAGTCAAAACTGGTGAGCGACTTTAGGAAAGATTTCCAGTTCTACAA
GGTCAGAGAGATCAACAACTACCACCATGCTCATGACGCATACCTGAACGCAGTGGTCGGGACT
GCCCTGATTAAGAAATACCCTAAACTGGAGTCTGAGTTCGTGTACGGCGACTATAAGGTGTACG
ATGTCAGAAAAATGATCGCCAAGAGCGAGCAGGAAATTGGCAAAGCCACCGCTAAGTATTTCTT
TTACTCCAACATCATGAATTTCTTTAAGACTGAGATCACCCTGGCAAATGGCGAAATCCGAAAG
AGGCCACTGATTGAGACTAACGGAGAGACaGGGGAAATCGTGTGGGACAAAGGAAGAGATTTTG

CTACCGTGCGGAAGGTCCTGAGTATGCCCCAAGTGAATATTGTCAAGAAAACAGAGGTGCAGAC
TGGAGGGTTCAGTAAGGAATCAATTCTGCCTAAACGCAACAGCGATAAGCTGATCGCCCGAAAG
AAAGACTGGGACCCCAAGAAGTATGGCGGATTCGACTCCCCAACCGTGGCTTACTCTGTCCTGG
TGGTCGCAAAGGTGGAGAAGGGAAAAAGCAAGAAACTGAAATCCGTCAAGGAACTGCTGGGGAT
CACAATTATGGAGAGGAGCAGCTTCGAAAAGAATCCTATCGATTTTCTGGAGGCCAAAGGGTAT
AAGGAAGTGAAGAAAGACCTGATCATCAAGCTGCCAAAGTACTCTCTGTTTGAGCTGGAAAACG
GCAGAAAGCGGATGCTGGCAAGTGCCGGCGAGCTGCAAAAAGGAAATGAACTGGCCCTGCCCTC
AAAGTACGTGAACTTCCTGTATCTGGCTAGCCACTACGAGAAGCTGAAAGGCTCCCCTGAGGAT
AACGAACAGAAACAGCTGTTTGTGGAGCAGCACAAGCATTATCTGGACGAGATCATTGAACAGA
TTAGCGAGTTCTCCAAACGCGTGATCCTGGCTGACGCAAATCTGGATAAGGTCCTGTCTGCATA
CAACAAACACAGGGACAAGCCAATCAGAGAGCAGGCCGAAAATATCATTCATCTGTTCACTCTG
ACCAACCTGGGAGCCCCCGCAGCCTTCAAGTATTTTGACACTACCATCGATCGCAAACGATACA
CAAGCACTAAGGAGGTGCTGGATGCTACCCTGATCCACCAGAGCATTACTGGGCTGTACGAGAC
AAGGATCGACCTGTCCCAGCTGGGGGGAGACAAACGCCCAGCCGCCACCAAGAAAGCAGGACAG
GCAAAGAAGAAGAAGTGA     (SEQ ID NO: 1)

FIG. 10 (continued, part 3 of 3)

```
Query   52  GACAAAAAGTATAGTATCGGACTGGATATTGGCACTAACAGCGTGGGATGGGCCGTCATC  111
Sbjct    4  GACAAGAAGTACTCCATTGGGCTCGATATCGGCACAAACAGCGTCGGCTGGGCCGTCATT   63

Query  112  ACCGACGAGTACAAAGTGCCAAGCAAGAAGTTCAAGGTCCTGGGAAACACCGATAGACAC  171
Sbjct   64  ACGGACGAGTACAAGGTGCCGAGCAAAAAATTCAAAGTTCTGGGCAATACCGATCGCCAC  123

Query  172  AGTATCAAGAAAAATCTGATTGGAGCCCTGCTGTTCGACTCAGGGGAGACAGCTGAAGCA  231
Sbjct  124  AGCATAAAGAAGAACCTCATTGGCGCCCTCCTGTTCGACTCCGGGGAGACGGCCGAAGCC  183

Query  232  ACTAGGCTGAAAAGAACAGCTAGGAGACGGTATACTCGCCGAAAGAATCGGATCTGCTAC  291
Sbjct  184  ACGCGGCTCAAAAGAACAGCACGGCGCAGATATACCCGCAGAAAGAATCGGATCTGCTAC  243

Query  292  CTCCAGGAGATTTTCTCCAACGAAATGGCCAAGGTGGACGATAGTTTCTTTCATCGCCTG  351
Sbjct  244  CTGCAGGAGATCTTTAGTAATGAGATGGCTAAGGTGGATGACTCTTTCTTCCATAGGCTG  303

Query  352  GAGGAATCATTCCTGGTCGAGGAAGATAAGAAACACGAGAGGCATCCCATCTTTGGCAAC  411
Sbjct  304  GAGGAGTCCTTTTTGGTGGAGGAGGATAAAAAGCACGAGCGCCACCCAATCTTTGGCAAT  363

Query  412  ATTGTGGACGAGGTCGCTTATCACGAAAAGTACCCTACAATCTATCATCTGCGGAAGAAA  471
Sbjct  364  ATCGTGGACGAGGTGGCGTACCATGAAAAGTACCCAACCATATATCATCTGAGGAAGAAG  423

Query  472  CTGGTGGACAGCACTGATAAGGCAGACCTGCGCCTGATCTATCTGGCCCTGGCTCACATG  531
Sbjct  424  CTTGTAGACAGTACTGATAAGGCTGACTTGCGGTTGATCTATCTCGCGCTGGCGCATATG  483

Query  532  ATTAAGTTCAGGGGGCATTTTCTGATCGAGGGCGATCTGAACCCAGACAATTCCGATGTG  591
Sbjct  484  ATCAAATTTCGGGGACACTTCCTCATCGAGGGGGACCTGAACCCAGACAACAGCGATGTC  543

Query  592  GACAAGCTGTTCATCCAGCTGGTCCAGACATACAATCAGCTGTTTGAGGAAAACCCCATT  651
Sbjct  544  GACAAACTCTTTATCCAACTGGTTCAGACTTACAATCAGCTTTTCGAAGAGAACCCGATC  603

Query  652  AATGCATCTGGGGTGGACGCAAAAGCCATCCTGAGTGCCAGACTGTCTAAGAGTAGGAGA  711
Sbjct  604  AACGCATCCGGAGTTGACGCCAAAGCAATCCTGAGCGCTAGGCTGTCCAAATCCCGGCGG  663

Query  712  CTGGAGAACCTGATCGCTCAGCTGCCAGGCGAAAAGAAAAACGGCCTGTTTGGAAATCTG  771
Sbjct  664  CTCGAAAACCTCATCGCACAGCTCCCTGGGGAGAAGAAGAACGGCCTGTTTGGTAATCTT  723
```

FIG. 11 (part 1 of 6, continued next page)

```
Query  772   ATTGCACTGTCACTGGGACTGACCCCCAACTTCAAGAGCAATTTTGATCTGGCCGAGGAC  831
             |||  | |||||||| ||| |||||||||||||  |   ||| ||| ||||||||| || 
Sbjct  724   ATCGCCCTGTCACTCGGGCTGACCCCCAACTTTAAATCTAACTTCGACCTGGCCGAAGAT  783

Query  832   GCTAAGCTCCAGCTGAGCAAGGACACCTACGACGATGACCTGGATAACCTGCTGGCTCAG  891
             || ||||| || ||||||||| ||||||||| ||||| || ||||| ||||||||| || 
Sbjct  784   GCCAAGCTTCAACTGAGCAAAGACACCTACGATGATGATCTCGACAATCTGCTGGCCCAG  843

Query  892   ATCGGCGATCAGTACGCAGACCTGTTCCTGGCCGCTAAGAATCTGTCTGACGCCATCCTG  951
             |||||||| ||||||||||||| |||  ||||  | |||||  ||||| ||||| | || 
Sbjct  844   ATCGGCGACCAGTACGCAGACCTTTTTTTGGCGGCAAAGAACCTGTCAGACGCCATTCTG  903

Query  952   CTGAGTGATATTCTGAGAGTGAACACCGAGATTACAAAAGCCCCCCTGTCAGCTAGCATG  1011
             |||||||||||||||| ||||||||| |||||| |||| ||||| ||| || |||| || 
Sbjct  904   CTGAGTGATATTCTGCGAGTGAACACGGAGATCACCAAAGCTCCGCTGAGCGCTAGTATG  963

Query  1012  ATCAAGAGATATGACGAGCACCATCAGGATCTGACCCTGCTGAAGGCTCTGGTGCGGCAG  1071
             ||||| | |||||||||||||||| || | |||||  ||||||||||  | ||| | || 
Sbjct  964   ATCAAGCGCTATGATGAGCACCACCAAGACTTGACTTTGCTGAAGGCCCTTGTCAGACAG  1023

Query  1072  CAGCTGCCTGAGAAGTACAAAGAAATCTTCTTTGATCAGAGCAAGAATGGGTACGCCGGC  1131
             ||  ||||||||||||||||||||||  ||| ||||||| ||| ||| |||||||||| 
Sbjct  1024  CAACTGCCTGAGAAGTACAAGGAAATTTTCTTCGATCAGTCTAAAAATGGCTACGCCGGA  1083

Query  1132  TATATTGACGGCGGAGCTTCCCAGGAGGAGTTCTACAAGTTTATCAAACCTATTCTGGAG  1191
             || || ||||||||||| |   ||||||| |||||||| ||| || ||| || ||||| 
Sbjct  1084  TACATTGACGGCGGAGCAAGCCAGGAGGAATTTTACAAATTTATTAAGCCCATCTTGGAA  1143

Query  1192  AAGATGGACGGCACTGAGGAACTGCTGGTGAAACTGAATCGGGAAGACCTGCTGCGGAAG  1251
             || |||||||||||  ||||| ||||||| ||| |  | |||| |  |||| | || || 
Sbjct  1144  AAAATGGACGGCACCGAGGAGCTGCTGGTAAAGCTTAACAGAGAAGATCTGTTGCGCAAA  1203

Query  1252  CAGCGCACCTTCGATAACGGCAGCATCCCTCACCAGATTCATCTGGGAGAGCTGCACGCA  1311
             ||||||||  | ||||| ||  ||||||| ||||||||||| ||||| ||  ||||||| 
Sbjct  1204  CAGCGCACTTTCGACAATGGAAGCATCCCCCACCAGATTCACCTGGGCGAACTGCACGCT  1263

Query  1312  ATCCTGCGGCGCCAGGAAGACTTCTACCCATTTCTGAAGGATAACCGGGAGAAGATCGAA  1371
             |||||  ||||||||||| ||||||||| || |||||| |||||| || || ||| || 
Sbjct  1264  ATCCTCAGGCGGCAAGAGGATTTCTACCCCTTTTTGAAAGATAACAGGGAAAAGATTGAG  1323

Query  1372  AAAATTCTGACTTTCCGCATCCCCTACTATGTGGGGCCTCTGGCAAGAGGCAATTCCCGG  1431
             ||||  || ||||||||||| ||||||||||  ||| || ||| ||||| ||||||| | 
Sbjct  1324  AAAATCCTCACATTTCGGATACCCTACTATGTAGGCCCCCTCGCCCGGGGAAATTCCAGA  1383

Query  1432  TTTGCCTGGATGACCCGCAAGTCTGAGGAAACAATCACTCCCTGGAACTTCGAGGAAGTG  1491
             || ||| |||||||| || ||||| ||||| ||||||||||||||||||||||||||||
Sbjct  1384  TTCGCGTGGATGACTCGCAAATCAGAAGAGACCATCACTCCCTGGAACTTCGAGGAAGTC  1443
```

FIG. 11 (continued, part 2 of 6)

```
Query  1492  GTCGATAAGGGCGCTTCCGCACAGTCTTTCATTGAGAGGATGACAAATTTTGACAAGAAC  1551
Sbjct  1444  GTGGATAAGGGGGCCTCTGCCCAGTCCTTCATCGAAAGGATGACTAACTTTGATAAAAAT  1503

Query  1552  CTGCCAAATGAAAAAGTGCTGCCCAAGCACAGCCTGCTGTACGAGTATTTCACCGTCTAT  1611
Sbjct  1504  CTGCCTAACGAAAAGGTGCTTCCTAAACACTCTCTGCTGTACGAGTACTTCACAGTTTAT  1563

Query  1612  AACGAACTGACAAAGGTGAAATACGTCACTGAGGGCATGAGAAAGCCTGCCTTCCTGTCC  1671
Sbjct  1564  AACGAGCTCACCAAGGTCAAATACGTCACAGAAGGGATGAGAAAGCCAGCATTCCTGTCT  1623

Query  1672  GGAGAACAGAAGAAAGCTATCGTGGACCTGCTGTTTAAAACCAATCGGAAGGTGACAGTC  1731
Sbjct  1624  GGAGAGCAGAAGAAAGCTATCGTGGACCTCCTCTTCAAGACGAACCGGAAAGTTACCGTG  1683

Query  1732  AAGCAGCTGAAAGAGGACTACTTCAAGAAAATTGAATGTTTCGATTCTGTGGAGATCAGT  1791
Sbjct  1684  AAACAGCTCAAAGAAGACTATTTCAAAAAGATTGAATGTTTCGACTCTGTTGAAATCAGC  1743

Query  1792  GGGGTCGAAGACAGGTTTAACGCCTCTCTGGGCACCTACCACGATCTGCTGAAGATCATT  1851
Sbjct  1744  GGAGTGGAGGATCGCTTCAACGCATCCCTGGGAACGTATCACGATCTCCTGAAAATCATT  1803

Query  1852  AAGGATAAAGACTTCCTGGACAACGAGGAAAATGAGGACATCCTGGAGGACATTGTGCTG  1911
Sbjct  1804  AAAGACAAGGACTTCCTGGACAATGAGGAGAACGAGGACATTCTTGAGGACATTGTCCTC  1863

Query  1912  ACCCTGACACTGTTTGAGGATCGGGAAATGATCGAGGAACGCCTGAAGACCTACGCCCAT  1971
Sbjct  1864  ACCCTTACGTTGTTTGAAGATAGGGAGATGATTGAAGAACGCTTGAAAACTTACGCTCAT  1923

Query  1972  CTGTTCGATGACAAAGTGATGAAACAGCTGAAGCGAAGGAGATACACTGGGTGGGGCCGA  2031
Sbjct  1924  CTCTTCGACGACAAAGTCATGAAACAGCTCAAGAGGCGCCGATATACAGGATGGGGGCGG  1983

Query  2032  CTGAGCAGGAAGCTGATCAATGGCATTCGCGACAAACAGAGTGGAAAGACAATCCTGGAC  2091
Sbjct  1984  CTGTCAAGAAAACTGATCAATGGGATCCGAGACAAGCAGAGTGGAAAGACAATCCTGGAT  2043

Query  2092  TTTCTGAAGTCAGATGGCTTCGCTAACAGGAATTTTATGCAGCTGATTCACGATGACTCT  2151
Sbjct  2044  TTTCTTAAGTCCGATGGATTTGCCAACCGGAACTTCATGCAGTTGATCCATGATGACTCT  2103

Query  2152  CTGACTTTCAAAGAGGACATCCAGAAGGCACAGGTGTCCGGACAGGGGGACTCTCTGCAC  2211
Sbjct  2104  CTCACCTTTAAGGAGGACATCCAGAAAGCACAAGTTTCTGGCCAGGGGACAGTCTTCAC  2163

Query  2212  GAGCATATCGCAAACCTGGCCGGGAGCCCTGCCATCAAGAAAGGCATCCTCCAGACCGTG  2271
Sbjct  2164  GAGCACATCGCTAATCTTGCAGGTAGCCCAGCTATCAAAAAGGGAATACTGCAGACCGTT  2223
```

FIG. 11 (continued, part 3 of 6)

```
Query  2272  AAGGTGGTGGACGAGCTGGTGAAAGTCATGGGAAGACATAAGCCAGAAAACATCGTGATT  2331
             ||||| |||||| ||| ||| ||||| ||||||| ||||||||| || ||||||| || 
Sbjct  2224  AAGGTCGTGGATGAACTCGTCAAAGTAATGGGAAGGCATAAGCCCGAGAATATCGTTATC  2283

Query  2332  GAGATGGCCAGGGAGAATCAGACCACACAGAAAGGGCAGAAGAACTCTCGGGAGCGCATG  2391
             ||||||||| |||||||  |   |  | ||||||| ||||||||| || ||| |  ||| 
Sbjct  2284  GAGATGGCCCGAGAGAACCAAACTACCCAGAAGGGACAGAAGAACAGTAGGGAAAGGATG  2343

Query  2392  AAACGCATCGAGGAAGGAATTAAGGAACTGGGGAGTCAGATCCTGAAAGAGCACCCCGTG  2451
             ||  | ||| ||||  |  || |||| ||||| | |||||||| |||||  ||||| | 
Sbjct  2344  AAGAGGATTGAAGAGGGTATAAAAGAACTGGGGTCCCAAATCCTTAAGGAACACCCAGTT  2403

Query  2452  GAAAACACACAGCTCCAGAATGAGAAGCTGTATCTGTACTACCTCCAGAATGGCCGCGAT  2511
             ||||||||  |||| ||||||||||||| | | ||||||||||| ||||| || | ||  
Sbjct  2404  GAAAACACCCAGCTTCAGAATGAGAAGCTCTACCTGTACTACCTGCAGAACGGCAGGGAC  2463

Query  2512  ATGTACGTGGACCAGGAGCTGGATATTAACCGACTGTCAGATTATGACGTGGATCATATC  2571
             ||||||||||| |||||  |||| || ||| | ||  | || |||||||||||||||||
Sbjct  2464  ATGTACGTGGATCAGGAACTGGACATCAATCGGCTCTCCGACTACGACGTGGATCATATC  2523

Query  2572  GTCCCACAGTCATTCCTGAAAGATGACAGCATTGACAATAAGGTGCTGACCCGCAGCGAC  2631
             || || |||||       ||||||||   |||||| ||||| || ||||  || | ||| 
Sbjct  2524  GTGCCCCAGTCTTTTCTCAAAGATGATTCTATTGATAATAAAGTGTTGACAAGATCCGAT  2583

Query  2632  AAAAACCGAGGAAAGAGTGATAATGTCCCCTCAGAGGAAGTGGTCAAGAAAATGAAGAAC  2691
             ||||      ||||||||||||| || || ||||| ||||| ||||||||||||| || 
Sbjct  2584  AAAAATAGAGGGAAGAGTGATAACGTCCCCTCAGAAGAAGTTGTCAAGAAAATGAAAAAT  2643

Query  2692  TACTGGAGGCAGCTGCTGAATGCCAAACTGATCACCCAGCGAAAGTTTGATAACCTGACA  2751
             || |||  ||||||||||||| |||||||||||||  |  || |||| |||| ||||| 
Sbjct  2644  TATTGGCGGCAGCTGCTGAACGCCAAACTGATCACACAACGGAAGTTCGATAATCTGACT  2703

Query  2752  AAAGCTGAGAGGGGGGGCCTGTCCGAACTGGACAAAGCAGGCTTCATCAAGCGACAGCTG  2811
             ||||||||  ||| ||||||||| |||  ||| ||||| ||||||||||| |||||||| 
Sbjct  2704  AAGGCTGAACGAGGTGGCCTGTCTGAGTTGGATAAAGCCGGCTTCATCAAAAGGCAGCTT  2763

Query  2812  GTGGAGACAAGGCAGATCACAAAGCACGTCGCTCAGATCCTGGACAGCAGGATGAACACC  2871
             || |||||| | ||||||||  ||||||| |  ||| ||| ||| |||| ||||||||| 
Sbjct  2764  GTTGAGACACGCCAGATCACCAAGCACGTGGCCCAAATTCTCGATTCACGCATGAACACC  2823

Query  2872  AAGTACGATGAGAATGACAAACTGATCCGGGAAGTGAAGGTCATTACACTGAAGTCAAAA  2931
             |||||||||||  ||||||||||||| |  || || ||  | |||| |||||||| ||  
Sbjct  2824  AAGTACGATGAAAATGACAAACTGATTCGAGAGGTGAAAGTTATTACTCTGAAGTCTAAG  2883

Query  2932  CTGGTGAGCGACTTTAGGAAAGATTTCCAGTTCTACAAGGTCAGAGAGATCAACAACTAC  2991
             ||||| || || ||| | |||||||| |||||  || |||| |||||||||||| || |
Sbjct  2884  CTGGTCTCAGATTTCAGAAAGGACTTTCAGTTTTATAAGGTGAGAGAGATCAACAATTAC  2943
```

FIG. 11 (continued, part 4 of 6)

```
Query  2992  CACCATGCTCATGACGCATACCTGAACGCAGTGGTCGGGACTGCCCTGATTAAGAAATAC  3051
             |||||||| ||| ||| ||||||||| ||||||||| |  ||||| || ||  |||||
Sbjct  2944  CACCATGCGCATGATGCCTACCTGAATGCAGTGGTAGGCACTGCACTTATCAAAAAATAT  3003

Query  3052  CCTAAACTGGAGTCTGAGTTCGTGTACGGCGACTATAAGGTGTACGATGTCAGAAAAATG  3111
             |  ||  ||||| |||| |||  ||||||| ||||||| |||||||||| || ||||||
Sbjct  3004  CCCAAGCTTGAATCTGAATTTGTTTACGGAGACTATAAAGTGTACGATGTTAGGAAAATG  3063

Query  3112  ATCGCCAAGAGCGAGCAGGAAATTGGCAAAGCCACCGCTAAGTATTTCTTTTACTCCAAC  3171
             ||||| || | ||||||||||||| ||||||||||||||||||| ||||||||| |||
Sbjct  3064  ATCGCAAAGTCTGAGCAGGAAATAGGCAAGGCCACCGCTAAGTACTTCTTTTACAGCAAT  3123

Query  3172  ATCATGAATTTCTTTAAGACTGAGATCACCCTGGCAAATGGCGAAATCCGAAAGAGGCCA  3231
             |  ||||||||  || ||||| |||| ||| ||||| |||  |||| | ||| | || |
Sbjct  3124  ATTATGAATTTTTTTCAAGACCGAGATTACACTGGCCAATGGAGAGATTCGGAAGCGACCA  3183

Query  3232  CTGATTGAGACTAACGGAGAGACAGGGGAAATCGTGTGGGACAAAGGAAGAGATTTTGCT  3291
             ||  | ||| |||| |||||| ||| ||||||||||||||||| ||  ||||||| |||
Sbjct  3184  CTTATCGAAACAAACGGAGAAACAGGAGAAATCGTGTGGGACAAGGGTAGGGATTTCGCG  3243

Query  3292  ACCGTGCGGAAGGTCCTGAGTATGCCCCAAGTGAATATTGTCAAGAAAACAGAGGTGCAG  3351
             ||  | |||||||||||| | ||||| ||||||| ||| |  |||||||| || ||||
Sbjct  3244  ACAGTCCGGAAGGTCCTGTCCATGCCGCAGGTGAACATCGTTAAAAAGACCGAAGTACAG  3303

Query  3352  ACTGGAGGGTTCAGTAAGGAATCAATTCTGCCTAAACGCAACAGCGATAAGCTGATCGCC  3411
             || ||||||  |   |||||| || |||  || || ||||||||||||||||||||| |
Sbjct  3304  ACCGGAGGCTTCTCCAAGGAAAAGTATCCTCCCGAAAAGGAACAGCGACAAGCTGATCGCA  3363

Query  3412  CGAAAGAAAGACTGGGACCCCAAGAAGTATGGCGGATTCGACTCCCCAACCGTGGCTTAC  3471
             ||||| ||| |  ||||||||||||| || ||||||||||  |  |||| || |||||
Sbjct  3364  CGCAAAAAAGATTGGGACCCCAAGAAATACGGCGGATTCGATTCTCCTACAGTCGCTTAC  3423

Query  3472  TCTGTCCTGGTGGTCGCAAAGGTGGAGAAGGGAAAAAGCAAGAAACTGAAATCCGTCAAG  3531
             |  || || || || ||||||||||||||||||  |||||||  |||||| || |||||
Sbjct  3424  AGTGTACTGGTTGTGGCCAAAGTGGAGAAAGGGAAGTCTAAAAAACTCAAAAGCGTCAAG  3483

Query  3532  GAACTGCTGGGGATCACAATTATGGAGAGGAGCAGCTTCGAAAAGAATCCTATCGATTTT  3591
             ||||||||||| ||||||||| |||||| ||||| |||||||||| |  |||||| |||
Sbjct  3484  GAACTGCTGGGCATCACAATCATGGAGCGATCAAGCTTCGAAAAAAACCCCATCGACTTT  3543

Query  3592  CTGGAGGCCAAAGGGTATAAGGAAGTGAAGAAAGACCTGATCATCAAGCTGCCAAAGTAC  3651
             ||  ||||| ||||| |||| |||| ||| ||||| |||||||| |||||  ||||||
Sbjct  3544  CTCGAGGCGAAAGGATATAAAGAGGTCAAAAAAGACCCTCATCATTAAGCTTCCCAAGTAC  3603

Query  3652  TCTCTGTTTGAGCTGGAAAACGGCAGAAAGCGGATGCTGGCAAGTGCCGGCGAGCTGCAA  3711
             ||||| |||||||| ||||||||| |||| |||| |  || |||||| ||||||||| |
Sbjct  3604  TCTCTCTTTGAGCTTGAAAACGGCCGGAAACGAATGCTCGCTAGTGCGGGCGAGCTGCAG  3663

Query  3712  AAAGGAAATGAACTGGCCCTGCCCTCAAAGTACGTGAACTTCCTGTATCTGGCTAGCCAC  3771
             ||||| || ||||||||||||||||| || |||||||| |||||||||||||| |||||
Sbjct  3664  AAAGGTAACGAGCTGGCACTGCCCTCTAAATACGTTAATTTCTTGTATCTGGCCAGCCAC  3723
```

FIG. 11 (continued, part 5 of 6)

```
Query  3772  TACGAGAAGCTGAAAGGCTCCCCTGAGGATAACGAACAGAAACAGCTGTTTGTGGAGCAG  3831
Sbjct  3724  TATGAAAAGCTCAAAGGGTCTCCCGAAGATAATGAGCAGAAGCAGCTGTTCGTGGAACAA  3783

Query  3832  CACAAGCATTATCTGGACGAGATCATTGAACAGATTAGCGAGTTCTCCAAACGCGTGATC  3891
Sbjct  3784  CACAAACACTACCTTGATGAGATCATCGAGCAAATAAGCGAATTCTCCAAAAGAGTGATC  3843

Query  3892  CTGGCTGACGCAAATCTGGATAAGGTCCTGTCTGCATACAACAAACACAGGGACAAGCCA  3951
Sbjct  3844  CTCGCCGACGCTAACCTCGATAAGGTGCTTTCTGCTTACAATAAGCACAGGGATAAGCCC  3903

Query  3952  ATCAGAGAGCAGGCCGAAAATATCATTCATCTGTTCACTCTGACCAACCTGGGAGCCCCC  4011
Sbjct  3904  ATCAGGGAGCAGGCAGAAAACATTATCCACTTGTTTACTCTGACCAACTTGGGCGCGCCT  3963

Query  4012  GCAGCCTTCAAGTATTTTGACACTACCATCGATCGCAAACGATACACAAGCACTAAGGAG  4071
Sbjct  3964  GCAGCCTTCAAGTACTTCGACACCACCATAGACAGAAAGCGGTACACCTCTACAAAGGAG  4023

Query  4072  GTGCTGGATGCTACCCTGATCCACCAGAGCATTACTGGGCTGTACGAGACAAGGATCGAC  4131
Sbjct  4024  GTCCTGGACGCCACACTGATTCATCAGTCAATTACGGGGCTCTATGAAACAAGAATCGAC  4083

Query  4132  CTGTCCCAGCTGGGGGGAGACA  4153     (SEQ ID NO: 2)
Sbjct  4084  CTCTCTCAGCTCGGTGGAGACA  4105     (SEQ ID NO: 3)
```

FIG. 11 (continued, part 6 of 6)

```
Query    1   ATGGCTCCCAAGAAGAAGCGAAAGGTGGGCATCCACGGCGTGCCCGCTGCCGACAAAAAG    60
             |||||  |||||||||||||| ||||||||| |||||||| ||||||| |||||| |||
Sbjct   70   ATGGCCCCAAAGAAGAAGCGGAAGGTCGGTATCCACGGAGTCCCAGCAGCCGACAAGAAG   129

Query   61   TATAGTATCGGACTGGATATTGGCACTAACAGCGTGGGATGGGCCGTCATCACCGACGAG   120
             ||||  ||||| |||||||| |||| ||| ||||| || |||||||||||||||||||
Sbjct  130   TACAGCATCGGCCTGGACATCGGCACCAACTCTGTGGGCTGGGCCGTGATCACCGACGAG   189

Query  121   TACAAAGTGCCAAGCAAGAAGTTCAAGGTCCTGGGAAACACCGATAGACACAGTATCAAG   180
             ||||| ||||| ||||||||| ||||||| ||||| ||||||||| || |||| |||||
Sbjct  190   TACAAGGTGCCCAGCAAGAAATTCAAGGTGCTGGGCAACACCGACCGGCACAGCATCAAG   249

Query  181   AAAAATCTGATTGGAGCCCTGCTGTTCGACTCAGGGGAGACAGCTGAAGCAACTAGGCTG   240
             ||  | ||||| |||||||||||||||||| | || |||||| ||| || || ||||||
Sbjct  250   AAGAACCTGATCGGAGCCCTGCTGTTCGACAGCGGCGAAACAGCCGAGGCCACCCGGCTG   309

Query  241   AAAAGAACAGCTAGGAGACGGTATACTCGCCGAAAGAATCGGATCTGCTACCTCCAGGAG   300
             ||  || || || || ||||||||||| |||| |||||| | ||||||| || ||||||
Sbjct  310   AAGAGAACCGCCAGAAGAAGATACACCAGACGGAAGAACCGGATCTGCTATCTGCAAGAG   369

Query  301   ATTTTCTCCAACGAAATGGCCAAGGTGGACGATAGTTTCTTTCATCGCCTGGAGGAATCA   360
             ||  | ||||| |||||||||||||||||||| ||  |||| || ||| |||||| |||
Sbjct  370   ATCTTCAGCAACGAGATGGCCAAGGTGGACGACAGCTTCTTCCACAGACTGGAAGAGTCC   429

Query  361   TTCCTGGTCGAGGAAGATAAGAAACACGAGAGGCATCCCATCTTTGGCAACATTGTGGAC   420
             ||||||||| ||||||||||||| |||||| || || |||||| || ||||||| ||||
Sbjct  430   TTCCTGGTGGAAGAGGATAAGAAGCACGAGCGGCACCCCATCTTCGGCAACATCGTGGAC   489

Query  421   GAGGTCGCTTATCACGAAAAGTACCCTACAATCTATCATCTGCGGAAGAAACTGGTGGAC   480
             ||||| || ||||||||||||||||| || ||||| || || || ||||||| |||||
Sbjct  490   GAGGTGGCCTACCACGAGAAGTACCCCACCATCTACCACCTGAGAAAGAAACTGGTGGAC   549

Query  481   AGCACTGATAAGGCAGACCTGCGCCTGATCTATCTGGCCCTGGCTCACATGATTAAGTTC   540
             |||||  ||||||| |||||||| ||||||||||||||||||| |||||||| |||||
Sbjct  550   AGCACCGACAAGGCCGACCTGCGGCTGATCTATCTGGCCCTGGCCCACATGATCAAGTTC   609

Query  541   AGGGGGCATTTTCTGATCGAGGGCGATCTGAACCCAGACAATTCCGATGTGGACAAGCTG   600
              ||||||| || ||||||||||||||  ||||||| |||||  | || ||||||||||||
Sbjct  610   CGGGGCCACTTCCTGATCGAGGGCGACCTGAACCCCGACAACAGCGACGTGGACAAGCTG   669

Query  601   TTCATCCAGCTGGTCCAGACATACAATCAGCTGTTTGAGGAAAACCCCATTAATGCATCT   660
             |||||||||||||| |||| ||||||||||||||| |||||||||||||| || ||| |
Sbjct  670   TTCATCCAGCTGGTGCAGACCTACAACCAGCTGTTCGAGGAAAACCCCATCAACGCCAGC   729

Query  661   GGGGTGGACGCAAAAGCCATCCTGAGTGCCAGACTGTCTAAGAGTAGGAGACTGGAGAAC   720
             || ||||||||||| |||||||| || |||||||||| ||||| ||||| |||||| |
Sbjct  730   GGCGTGGACGCCAAGGCCATCCTGTCTGCCAGACTGAGCAAGAGCAGACGGCTGGAAAAT   789
```

FIG. 12 (part 1 of 6, continued next page)

```
Query   721  CTGATCGCTCAGCTGCCAGGCGAAAAGAAAAACGGCCTGTTTGGAAATCTGATTGCACTG  780
Sbjct   790  CTGATCGCCCAGCTGCCCGGCGAGAAGAAGAATGGCCTGTTCGGCAACCTGATTGCCCTG  849

Query   781  TCACTGGGACTGACCCCCAACTTCAAGAGCAATTTTGATCTGGCCGAGGACGCTAAGCTC  840
Sbjct   850  AGCCTGGGCCTGACCCCCAACTTCAAGAGCAACTTCGACCTGGCCGAGGATGCCAAACTG  909

Query   841  CAGCTGAGCAAGGACACCTACGACGATGACCTGGATAACCTGCTGGCTCAGATCGGCGAT  900
Sbjct   910  CAGCTGAGCAAGGACACCTACGACGACGACCTGGACAACCTGCTGGCCCAGATCGGCGAC  969

Query   901  CAGTACGCAGACCTGTTCCTGGCCGCTAAGAATCTGTCTGACGCCATCCTGCTGAGTGAT  960
Sbjct   970  CAGTACGCCGACCTGTTTCTGGCCGCCAAGAACCTGTCCGACGCCATCCTGCTGAGCGAC  1029

Query   961  ATTCTGAGAGTGAACACCGAGATTACAAAAGCCCCCCTGTCAGCTAGCATGATCAAGAGA  1020
Sbjct  1030  ATCCTGAGAGTGAACACCGAGATCACCAAGGCCCCCCTGAGCGCCTCTATGATCAAGAGA  1089

Query  1021  TATGACGAGCACCATCAGGATCTGACCCTGCTGAAGGCTCTGGTGCGGCAGCAGCTGCCT  1080
Sbjct  1090  TACGACGAGCACCACCAGGACCTGACCCTGCTGAAAGCTCTCGTGCGGCAGCAGCTGCCT  1149

Query  1081  GAGAAGTACAAAGAAATCTTCTTTGATCAGAGCAAGAATGGGTACGCCGGCTATATTGAC  1140
Sbjct  1150  GAGAAGTACAAAGAGATTTTCTTCGACCAGAGCAAGAACGGCTACGCCGGCTACATTGAC  1209

Query  1141  GGCGGAGCTTCCCAGGAGGAGTTCTACAAGTTTATCAAACCTATTCTGGAGAAGATGGAC  1200
Sbjct  1210  GGCGGAGCCAGCCAGGAAGAGTTCTACAAGTTCATCAAGCCCATCCTGGAAAAGATGGAC  1269

Query  1201  GGCACTGAGGAACTGCTGGTGAAACTGAATCGGGAAGACCTGCTGCGGAAGCAGCGCACC  1260
Sbjct  1270  GGCACCGAGGAACTGCTCGTGAAGCTGAACAGAGAGGACCTGCTGCGGAAGCAGCGGACC  1329

Query  1261  TTCGATAACGGCAGCATCCCTCACCAGATTCATCTGGGAGAGCTGCACGCAATCCTGCGG  1320
Sbjct  1330  TTCGACAACGGCAGCATCCCCCACCAGATCCACCTGGGAGAGCTGCACGCCATTCTGCGG  1389

Query  1321  CGCCAGGAAGACTTCTACCCATTTCTGAAGGATAACCGGGAGAAGATCGAAAAAATTCTG  1380
Sbjct  1390  CGGCAGGAAGATTTTTACCCATTCCTGAAGGACAACCGGGAAAAGATCGAGAAGATCCTG  1449

Query  1381  ACTTTCCGCATCCCCTACTATGTGGGGCCTCTGGCAAGAGGCAATTCCCGGTTTGCCTGG  1440
Sbjct  1450  ACCTTCCGCATCCCCTACTACGTGGGCCCTCTGGCCAGGGGAAACAGCAGATTCGCCTGG  1509
```

```
Query  1441  ATGACCCGCAAGTCTGAGGAAACAATCACTCCCTGGAACTTCGAGGAAGTGGTCGATAAG  1500
             ||||||  |||| || ||||||| ||||||| ||  ||||||||||||||||||| |||
Sbjct  1510  ATGACCAGAAAGAGCGAGGAAACCATCACCCCCTGGAACTTCGAGGAAGTGGTGGACAAG  1569

Query  1501  GGCGCTTCCGCACAGTCTTTCATTGAGAGGATGACAAATTTTGACAAGAACCTGCCAAAT  1560
             ||||||||||| ||||| |||| ||| |||||||||| |||||| ||||||||||||| |
Sbjct  1570  GGCGCTTCCGCCCAGAGCTTCATCGAGCGGATGACCAACTTCGATAAGAACCTGCCCAAC  1629

Query  1561  GAAAAAGTGCTGCCCAAGCACAGCCTGCTGTACGAGTATTTCACCGTCTATAACGAACTG  1620
             ||| | |||||||||||||||||||||||||||||||| ||||||||| |||||| |||
Sbjct  1630  GAGAAGGTGCTGCCCAAGCACAGCCTGCTGTACGAGTACTTCACCGTGTATAACGAGCTG  1689

Query  1621  ACAAAGGTGAAATACGTCACTGAGGGCATGAGAAAGCCTGCCTTCCTGTCCGGAGAACAG  1680
             || |||||||||||||| || ||||| |||||||||||||||||||| | |||||||||
Sbjct  1690  ACCAAAGTGAAATACGTGACCGAGGGAATGAGAAAGCCCGCCTTCCTGAGCGGCGAGCAG  1749

Query  1681  AAGAAAGCTATCGTGGACCTGCTGTTTAAAACCAATCGGAAGGTGACAGTCAAGCAGCTG  1740
             || ||||| |||||||||||||||||| || |||||| ||||| |||| || ||||||
Sbjct  1750  AAAAAGGCCATCGTGGACCTGCTGTTCAAGACCAACCGGAAAGTGACCGTGAAGCAGCTG  1809

Query  1741  AAAGAGGACTACTTCAAGAAAATTGAATGTTTCGATTCTGTGGAGATCAGTGGGGTCGAA  1800
             ||||||||||||||||||||| || || || |||| ||||||||||| ||||||| |||
Sbjct  1810  AAAGAGGACTACTTCAAGAAAATCGAGTGCTTCGACTCCGTGGAAATCTCCGGCGTGGAA  1869

Query  1801  GACAGGTTTAACGCCTCTCTGGGCACCTACCACGATCTGCTGAAGATCATTAAGGATAAA  1860
             || ||||| ||||||| |||||||| ||||||||||||||||| | |||||||||| ||
Sbjct  1870  GATCGGTTCAACGCCTCCCTGGGCACATACCACGATCTGCTGAAAATTATCAAGGACAAG  1929

Query  1861  GACTTCCTGGACAACGAGGAAAATGAGGACATCCTGGAGGACATTGTGCTGACCCTGACA  1920
             ||||||||||||||| |||||||| ||||||| ||||| ||||| ||||||||||||||
Sbjct  1930  GACTTCCTGGACAATGAGGAAAACGAGGACATTCTGGAAGATATCGTGCTGACCCTGACA  1989

Query  1921  CTGTTTGAGGATCGGGAAATGATCGAGGAACGCCTGAAGACCTACGCCCATCTGTTCGAT  1980
             ||||||||||| || || ||||||||||||||| ||||| |||||||||| |||||||
Sbjct  1990  CTGTTTGAGGACAGAGAGATGATCGAGGAACGGCTGAAAACCTATGCCCACCTGTTCGAC  2049

Query  1981  GACAAAGTGATGAAACAGCTGAAGCGAAGGAGATACACTGGGTGGGGCCGACTGAGCAGG  2040
             ||||||||||||| |||||||||||| || ||||||| ||||||||| |||||||||
Sbjct  2050  GACAAAGTGATGAAGCAGCTGAAGCGGCGGAGATACACCGGCTGGGGCAGGCTGAGCCGG  2109

Query  2041  AAGCTGATCAATGGCATTCGCGACAAACAGAGTGGAAAGACAATCCTGGACTTTCTGAAG  2100
             |||||||||||| ||||| | |||||||||||||| || |||||||||||| ||||||
Sbjct  2110  AAGCTGATCAACGGCATCCGGGACAAGCAGTCCGGCAAGACAATCCTGGATTTCCTGAAG  2169

Query  2101  TCAGATGGCTTCGCTAACAGGAATTTTATGCAGCTGATTCACGATGACTCTCTGACTTTC  2160
             || ||||||||||| |||||| |||||||||||||||| |||| ||||| |||||||||
Sbjct  2170  TCCGACGGCTTCGCCAACAGAAACTTCATGCAGCTGATCCACGACGACAGCCTGACCTTT  2229
```

FIG. 12 (continued, part 3 of 6)

```
Query  2161  AAAGAGGACATCCAGAAGGCACAGGTGTCCGGACAGGGGGACTCTCTGCACGAGCATATC  2220
             |||||||||||||||||||| ||||||||||||| ||||  |||||||||||||||| |
Sbjct  2230  AAAGAGGACATCCAGAAAGCCCAGGTGTCCGGCCAGGGCGATAGCCTGCACGAGCACATT  2289

Query  2221  GCAAACCTGGCCGGGAGCCCTGCCATCAAGAAAGGCATCCTCCAGACCGTGAAGGTGGTG  2280
             ||||  ||||||||| |||| ||||| |||||| ||||||| ||||| |||||||||||
Sbjct  2290  GCCAATCTGGCCGGCAGCCCCGCCATTAAGAAGGGCATCCTGCAGACAGTGAAGGTGGTG  2349

Query  2281  GACGAGCTGGTGAAAGTCATGGGAAGACATAAGCCAGAAAACATCGTGATTGAGATGGCC  2340
             |||||||| ||||||| |||||| | ||| ||||| ||||||||||||||| ||||||| 
Sbjct  2350  GACGAGCTCGTGAAAGTGATGGGCCGGCACAAGCCCGAGAACATCGTGATCGAAATGGCC  2409

Query  2341  AGGGAGAATCAGACCACACAGAAAGGGCAGAAGAACTCTCGGGAGCGCATGAAACGCATC  2400
             || || || |||||||| ||||||||||||||||| | ||| ||| |||||| | | ||
Sbjct  2410  AGAGAGAACCAGACCACCCAGAAGGGACAGAAGAACAGCCGCGAGAGAATGAAGCGGATC  2469

Query  2401  GAGGAAGGAATTAAGGAACTGGGGAGTCAGATCCTGAAAGAGCACCCCGTGGAAAACACA  2460
             ||||| || ||||| ||||||| || |||||||||||||||  ||||||||||||||| 
Sbjct  2470  GAAGAGGGCATCAAAGAGCTGGGCAGCCAGATCCTGAAAGAACACCCCGTGGAAAACACC  2529

Query  2461  CAGCTCCAGAATGAGAAGCTGTATCTGTACTACCTCCAGAATGGCCGCGATATGTACGTG  2520
             |||||| ||||||||||||||||  |||||||||| |||||||||  ||||||||||||
Sbjct  2530  CAGCTGCAGAACGAGAAGCTGTACCTGTACTACCTGCAGAATGGGCGGGATATGTACGTG  2589

Query  2521  GACCAGGAGCTGGATATTAACCGACTGTCAGATTATGACGTGGATCATATCGTCCCACAG  2580
             |||||||| ||||| || ||||| ||||| || || ||||||||||||||||| || ||
Sbjct  2590  GACCAGGAACTGGACATCAACCGGCTGTCCGACTACGATGTGGACCATATCGTGCCTCAG  2649

Query  2581  TCATTCCTGAAAGATGACAGCATTGACAATAAGGTGCTGACCCGCAGCGACAAAAACCGA  2640
              |  |||| ||| || ||| |||| ||||||||||||||||| ||||||||||| || |
Sbjct  2650  AGCTTTCTGAAGGACGACTCCATCGACAACAAGGTGCTGACCAGAAGCGACAAGAACCGG  2709

Query  2641  GGAAAGAGTGATAATGTCCCCTCAGAGGAAGTGGTCAAGAAAATGAAGAACTACTGGAGG  2700
             | ||| || |||||||| ||  | ||| |||| |||||| ||||||||||||||||| |
Sbjct  2710  GCAAGAGCGACAACGTGCCCTCCGAAGAGGTCGTGAAGAAGATGAAGAACTACTGGCGG  2769

Query  2701  CAGCTGCTGAATGCCAAACTGATCACCCAGCGAAAGTTTGATAACCTGACAAAAGCTGAG  2760
             |||||||||||||| ||| |||| || ||| | ||||| ||||| ||||| ||| ||||
Sbjct  2770  CAGCTGCTGAACGCCAAGCTGATTACCCAGAGAAAGTTCGACAATCTGACCAAGGCCGAG  2829

Query  2761  AgggggggCCTGTCCGAACTGGACAAAGCAGGCTTCATCAAGCGACAGCTGGTGGAGACA  2820
             || || || ||| || ||||||||||| |||||||||||||| ||||||||||||| ||
Sbjct  2830  AGAGGCGGCCTGAGCGAACTGGATAAGGCCGGCTTCATCAAGAGACAGCTGGTGGAAACC  2889

Query  2821  AGGCAGATCACAAAGCACGTCGCTCAGATCCTGGACAGCAGGATGAACACCAAGTACGAT  2880
             ||||||||||||||||||||| | |||||||||||| || |||||||| || |||||| 
Sbjct  2890  CGGCAGATCACAAAGCACGTGGCACAGATCCTGGACTCCCGGATGAACACTAAGTACGAC  2949
```

FIG. 12 (continued, part 4 of 6)

```
Query  2881  GAGAATGACAAACTGATCCGGGAAGTGAAGGTCATTACACTGAAGTCAAAACTGGTGAGC  2940
             |||||||||||| ||||||||||||||||| ||||| ||| |||||||| ||||||| |
Sbjct  2950  GAGAATGACAAGCTGATCCGGGAAGTGAAAGTGATCACCCTGAAGTCCAAGCTGGTGTCC  3009

Query  2941  GACTTTAGGAAAGATTTCCAGTTCTACAAGGTCAGAGAGATCAACAACTACCACCATGCT  3000
             ||  | ||||| ||||||||||| |||||||| | ||||||||||||||||||||| ||
Sbjct  3010  GATTTCCGGAAGGATTTCCAGTTTTACAAAGTGCGCGAGATCAACAACTACCACCACGCC  3069

Query  3001  CATGACGCATACCTGAACGCAGTGGTCGGGACTGCCCTGATTAAGAAATACCCTAAACTG  3060
             ||  ||||  ||||||||||| | ||||||  || ||||||| |||| |||||||||||
Sbjct  3070  CACGACGCCTACCTGAACGCCGTCGTGGGAACCGCCCTGATCAAAAAGTACCCTAAGCTG  3129

Query  3061  GAGTCTGAGTTCGTGTACGGCGACTATAAGGTGTACGATGTCAGAAAAATGATCGCCAAG  3120
             ||   |||||||||||||||||||| |||||||||||  ||| |||| |||||||||||
Sbjct  3130  GAAAGCGAGTTCGTGTACGGCGACTACAAGGTGTACGACGTGCGGAAGATGATCGCCAAG  3189

Query  3121  AGCGAGCAGGAAATTGGCAAAGCCACCGCTAAGTATTTCTTTTACTCCAACATCATGAAT  3180
             ||||||||||||||| ||||||| |||||||||||||||||| |||| ||||||||||
Sbjct  3190  AGCGAGCAGGAAATCGGCAAGGCTACCGCCAAGTACTTCTTCTACAGCAACATCATGAAC  3249

Query  3181  TTCTTTAAGACTGAGATCACCCTGGCAAATGGCGAAATCCGAAAGAGGCCACTGATTGAG  3240
             |  ||||||||| ||||| |||||||||| || ||||| || ||||| || |||| ||
Sbjct  3250  TTTTTCAAGACCGAGATTACCCTGGCCAACGGCGAGATCCGGAAGCGGCCTCTGATCGAG  3309

Query  3241  ACTAACGGAGAGACAGGGGAAATCGTGTGGGACAAAGGAAGAGATTTTGCTACCGTGCGG  3300
             ||   ||| ||| | || ||| |||||||||||  || ||||| ||||||||||||||
Sbjct  3310  ACAAACGGCGAAACCGGGGAGATCGTGTGGGATAAGGGCCGGGATTTTGCCACCGTGCGG  3369

Query  3301  AAGGTCCTGAGTATGCCCCAAGTGAATATTGTCAAGAAAACAGAGGTGCAGACTGGAGGG  3360
             ||||| ||||| ||||||||||||||||| |||| ||||| |||||||||||| |  |
Sbjct  3370  AAAGTGCTGAGCATGCCCCAAGTGAATATCGTGAAAAAGACCGAGGTGCAGACAGGCGGC  3429

Query  3361  TTCAGTAAGGAATCAATTCTGCCTAAACGCAACAGCGATAAGCTGATCGCCCGAAAGAAA  3420
             |||||| ||||| | ||||| |||||| |||||||||||||||||||||| | ||||| 
Sbjct  3430  TTCAGCAAAGAGTCTATCCTGCCCAAGAGGAACAGCGATAAGCTGATCGCCAGAAAGAAG  3489

Query  3421  GACTGGGACCCCAAGAAGTATGGCGGATTCGACTCCCCAACCGTGGCTTACTCTGTCCTG  3480
             ||||||||||| |||||||| ||||| |||||| | ||||||||||| || ||||| ||
Sbjct  3490  GACTGGGACCCTAAGAAGTACGGCGGCTTCGACAGCCCCACCGTGGCCTATTCTGTGCTG  3549

Query  3481  GTGGTCGCAAAGGTGGAGAAGGGAAAAAGCAAGAAACTGAAATCCGTCAAGGAACTGCTG  3540
             |||| ||| ||||||| ||||| |||| ||||| ||||||  | |||||| ||||||||
Sbjct  3550  GTGGTGGCCAAAGTGGAAAAGGGCAAGTCCAAGAAACTGAAGAGTGTGAAAGAGCTGCTG  3609

Query  3541  GGGATCACAATTATGGAGAGGAGCAGCTTCGAAAAGAATCCTATCGATTTTCTGGAGGCC  3600
             |||||||| || ||||| || |||||||||||||||||||| ||||| |||||| |||
Sbjct  3610  GGGATCACCATCATGGAAAGAAGCAGCTTCGAGAAGAATCCCATCGACTTTCTGGAAGCC  3669
```

```
Query  3601  AAAGGGTATAAGGAAGTGAAGAAAGACCTGATCATCAAGCTGCCAAAGTACTCTCTGTTT  3660
Sbjct  3670  AAGGGCTACAAAGAAGTGAAAAAGGACCTGATCATCAAGCTGCCTAAGTACTCCCTGTTC  3729

Query  3661  GAGCTGGAAAACGGCAGAAAGCGGATGCTGGCAAGTGCCGGCGAGCTGCAAAAAGGAAAT  3720
Sbjct  3730  GAGCTGGAAAACGGCCGGAAGAGAATGCTGGCCTCTGCCGGCGAACTGCAGAAGGGAAAC  3789

Query  3721  GAACTGGCCCTGCCCTCAAAGTACGTGAACTTCCTGTATCTGGCTAGCCACTACGAGAAG  3780
Sbjct  3790  GAACTGGCCCTGCCCTCCAAATATGTGAACTTCCTGTACCTGGCCAGCCACTATGAGAAG  3849

Query  3781  CTGAAAGGCTCCCCTGAGGATAACGAACAGAAACAGCTGTTTGTGGAGCAGCACAAGCAT  3840
Sbjct  3850  CTGAAGGGCTCCCCCGAGGATAATGAGCAGAAACAGCTGTTTGTGGAACAGCACAAGCAC  3909

Query  3841  TATCTGGACGAGATCATTGAACAGATTAGCGAGTTCTCCAAACGCGTGATCCTGGCTGAC  3900
Sbjct  3910  TACCTGGACGAGATCATCGAGCAGATCAGCGAGTTCTCCAAGAGAGTGATCCTGGCCGAC  3969

Query  3901  GCAAATCTGGATAAGGTCCTGTCTGCATACAACAAACACAGGGACAAGCCAATCAGAGAG  3960
Sbjct  3970  GCTAATCTGGACAAAGTGCTGTCCGCCTACAACAAGCACCGGGATAAGCCCATCAGAGAG  4029

Query  3961  CAGGCCGAAAATATCATTCATCTGTTCACTCTGACCAACCTGGGAGCCCCCGCAGCCTTC  4020
Sbjct  4030  CAGGCCGAGAATATCATCCACCTGTTTACCCTGACCAATCTGGGAGCCCCTGCCGCCTTC  4089

Query  4021  AAGTATTTTGACACTACCATCGATCGCAAACGATACACAAGCACTAAGGAGGTGCTGGAT  4080
Sbjct  4090  AAGTACTTTGACACCACCATCGACCGGAAGAGGTACACCAGCACCAAAGAGGTGCTGGAC  4149

Query  4081  GCTACCCTGATCCACCAGAGCATTACTGGGCTGTACGAGACAAGGATCGACCTGTCCCAG  4140
Sbjct  4150  GCCACCCTGATCCACCAGAGCATCACCGGCCTGTACGAGACACGGATCGACCTGTCTCAG  4209

Query  4141  CTGGGGGGAGACAAACGCCCAGCCGCCACCAAGAAAGCAGGACAGGCAAAGAAGAAGAAG  4200
Sbjct  4210  CTGGGAGGCGACAAGCGTCCTGCTGCTACTAAGAAAGCTGGTCAAGCTAAGAAAAAGAAA  4269

Query  4201  TGA  4203    (SEQ ID NO: 4)
Sbjct  4270  TGA  4272    (SEQ ID NO: 5)
```

FIG. 12 (continued, part 6 of 6)

COMPOSITIONS AND METHODS DIRECTED TO CRISPR/CAS GENOMIC ENGINEERING SYSTEMS

CROSS-REFERENCE TO RELATED APPLICATIONS

This application claims benefit of U.S. Provisional Application Ser. No. 61/799,586, filed in the United States Patent and Trademark Office on Mar. 15, 2013, which is herein incorporated by reference in its entirety.

SEQUENCE LISTING

The instant application contains a Sequence Listing which has been submitted electronically in ASCII format and is hereby incorporated by reference in its entirety. Said ASCII copy, created on May 8, 2014, is named 1458.03NPR_SL.txt and is 31,454 bytes in size.

FIELD OF THE INVENTION

The invention relates generally to systems for targeted genomic modification in mammalian cells.

BACKGROUND OF THE INVENTION

Small RNA-based defense systems that provide adaptive, heritable immunity against viruses, plasmids, and other mobile genetic elements have recently been discovered in archaea and bacteria. The RNA and protein components of these immune systems arise from the CRISPR (clustered regularly interspaced short palindromic repeat) and Cas (CRISPR-associated) genes, respectively. CRISPR locus consists of variable similar sized, short regions (spacers) that separate each of short repeats. The spacers are mainly homologous to the invading sequences and the repeats are identical sequences. Cas genes are often located adjacent to the CRISPR locus. Prokaryotes with CRISPR-Cas immune systems capture short invader sequences with the CRISPR loci in the genomes, and small RNAs produced from the CRISPR loci (crRNAs) guide Cas proteins to recognize and degrade (or otherwise silence) the invading nucleic acids.

CRISPR-Cas systems operate through three general steps to provide immunity: adaptation, crRNA biogenesis, and invader silencing. In the adaptation phase, a short fragment of foreign DNA (protospacer) is acquired from the invader and integrated into the host CRISPR locus adjacent to the leader. Protospacer adjacent motifs (PAMs) are found near invader sequences selected for CRISPR integration.

In the crRNA biogenesis phase, CRISPR locus transcripts are processed to release a set of small individual mature crRNAs (each targeting a different sequence). Mature crRNA generally retain some of the repeat sequence, which is thought to provide a recognizable signature of the crRNA. In the silencing phase, crRNA-Cas protein complexes recognize and degrade foreign DNAs or RNAs.

There are three types of CRISP-Cas systems. Type II CRISPR-Cas systems has been extensively studied partially because they offered practical applications in the dairy industry to generate phage-resistant *Streptococcus thermophilus* (*S. thermophilus*) strains. In addition to its content and architecture, Type II systems also differ from other types in the biogenesis of crRNA. A set of small non-coding RNAs called tracrRNA (trans-activating CRISPR RNA) are produced from a region outside but close to the CRISPR locus. The tracrRNAs are partially complementary to the type II CRISPR repeat sequences and hybridize to the repeats within the long precursor CRISPR RNA and the RNA duplexes are processed by non-CRISPR RNase III to generate mature crRNAs. Cas9, a large type II signature protein, is thought to be the only protein involved in the crRNA-guided silencing of foreign nucleic acids.

Jinek et al. "A Programmable Dual-RNA-Guided DNA Endonuclease in Adaptive Bacterial Immunity," Science 337 (6096), p. 816-821 (August 2012) show that crRNA fused to a tracrRNA (called crRNA-tracrRNA chimera or guide chimeric RNAs) is sufficient to direct Cas9 protein to sequence-specifically cleave target DNA sequences matching the crRNA using in vitro reconstitution of *Streptococcus pyogenes* (*S. pyogenes*) type II CRISPR system. However, the study was based on biochemical assays and did not show whether or not the Cas9-crRNA-tracrRNA system would work in the cells of eukaryotic organisms.

To explore the potential of RNA-programmed Cas9 for genome-editing applications in mammalian cells, Mali et al., "RNA-Guided Human Genome Engineering via Cas9" Science Express (Jan. 3, 2013) and Cong et al., "Multiplex Genome Engineering Using CRISPR/Cas Systems" Science Express (Jan. 3, 2013) independently engineer Cas9 and RNA components of the bacterial type II CRISPR system in human cells and/or mouse cells. Both labs were able to introduce precise double stranded break at endogenous genomic loci in human cells and/or mouse cells using human codon-optimized version of the *S. pyogenes* Cas9 proteins directed by short RNAs. The two labs designed and used different nucleic acid sequences to encode codon-optimized *S. pyogenes* Cas9 protein.

RNA-guided genome targeting defines a potential new class of genome engineering tools. What is needed in the art are efficient and versatile methods and tools for RNA-programmed genome engineering. Improved efficient systems using RNA-programmed Cas9 can be used, for example, to study biology by perturbing gene networks, and also for example, can be used to treat genetic diseases by repairing genetic defects or by reintroducing genes into cells.

SUMMARY OF THE INVENTION

The present disclosure provides an all-in-one CRISPR II system for genomic modification comprising (i) an polynucleotide encoding the *S. pyogenes* Cas9 protein, and (ii) guide-RNAs for RNA-guided genome engineering in human or mouse cells. The present specification describes the design, expression and testing of a polynucleotide that has been optimized for expression of *S. pyogenes* Cas9 protein in mammalian cells such as human or mouse cells, and describes the testing of the all-in-one system for RNA-guided genome engineering in human cells. The disclosure further provides human codon-optimized polynucleotides encoding a *S. pyogenes* Cas9 protein where the protein also bears an N terminal myc-tag and two nuclear localization signals (NLS), located in the N-terminus and C-terminus, respectively.

BRIEF DESCRIPTION OF THE DRAWINGS

FIG. 1B provides nucleotide sequences and other information describing the guide sequence insertion site in the all-in-one CRISPRII system expression construct.

FIG. 1C provides the general form of the target guide sequence to be used in the all-in-one CRISPR II system expression construct.

FIG. 3A provides a schematic of the expression construct EF1-hspCas9-H1-AAVS.

FIG. 3B provides a schematic of an expression construct EF1-spCas9-mcherry-H1-AAVS.

FIG. 3C provides the nucleotide sequence of the AAVS target sequence (SEQ ID NO: 11).

FIG. 4 provides fluorescent images of EGIP-293T cells following transfection of alternatively three expression constructs along with donor, and cells transfected with donor alone.

FIG. 5 provides a photograph of the results of a SUR-VEYOR® Mutation Detection Kit assay, measuring cleavage activity.

FIG. 6A provides a schematic of an expression construct EF1-hspCas9-H1-Luc.

FIG. 6B provides the nucleotide sequences of two gRNAs that target the luciferase sequence.

FIG. 6C provides a schematic of homologous recombination event that takes place in a luciferase stable reporter cell line.

FIG. 10 provides the nucleotide sequence (SEQ ID NO: 1) of the human codon-optimized polynucleotide encoding the *S. pyogenes* Cas9 protein (hspCas9) further comprising an N-terminal myc-tag and two nuclear localization signals.

FIG. 11 provides a nucleotide sequence alignment of the polynucleotides of two cas9 sequences, where the query sequence is the hspCas9 domain of the present invention, containing only the Cas9 coding region, without sequences encoding the myc-tag or NLS, i.e., the query sequence is nucleotide positions 91 through 4191 of the nucleotide sequence provided in FIG. 10 and SEQ ID NO: 2. The subject sequence is a cas9 sequence of Mali et al., "RNA-Guided Human Genome Engineering via Cas9," Science Express (Jan. 3, 2013); SEQ ID NO: 3.

FIG. 12 provides a nucleotide sequence alignment of the polynucleotides of two cas9 sequences, where the query sequence is the hspCas9 domain containing the N-terminal and C-terminal NLS, and without sequences encoding the myc-tag, i.e., the query sequence is nucleotide positions 40 through 4242 of the nucleotide sequence provided in FIG. 10 and SEQ ID NO: 4. The subject sequence is a cas9 sequence of Cong et al., "Multiplex Genome Engineering Using CRISPR/Cas Systems," Science Express (Jan. 3, 2013); SEQ ID NO: 5.

DETAILED DESCRIPTION OF THE INVENTION

Figure 1A:
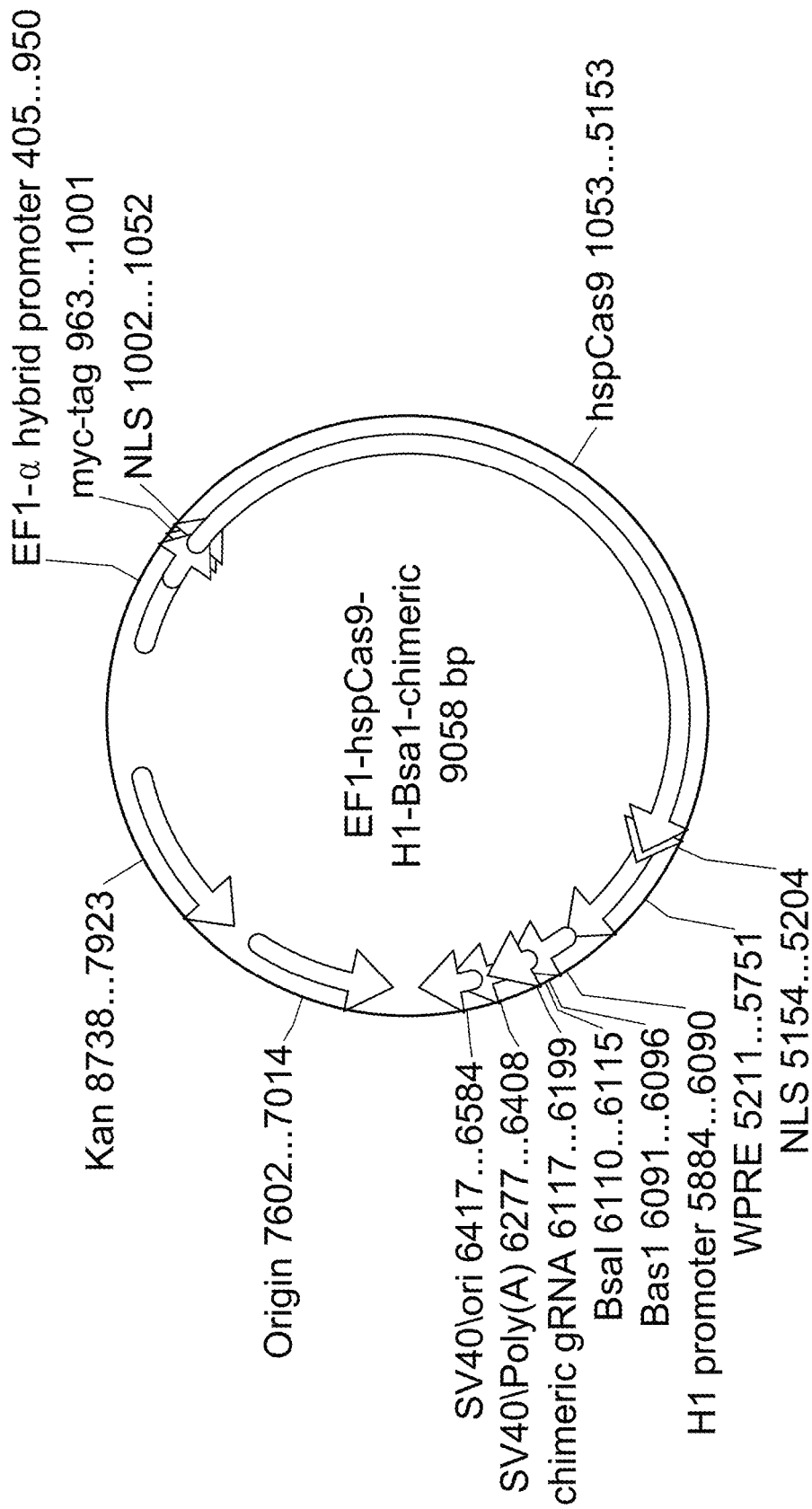
FIG. 1A provides a map of the mammalian expression construct for use with the all-in-one CRISPRII system.

In one aspect, the present disclosure provides a human codon-optimized polynucleotide encoding the *S. pyogenes* Cas9 protein bearing an N terminus Myc tag and two nuclear localization signals (NLS), located in the N terminus and C terminus, respectively. The disclosure also provides all-in-one CRISPR II systems with prokaryote encoded Cas9 that is also able achieve genomic editing in mammalian cells.

Taken together, the present disclosure demonstrates that an engineered all-in-one CRISPR II system is able to achieve genomic targeting and modification in a simple, flexible and highly efficient way. Combination of two or more all-in-one CRISPR II systems with different gRNAs would also allow effective multiplex genome editing.

The all-in-one CRISPR II system has a wide variety of potential applications across basic sciences, biotechnology and biomedicine.

To accommodate the wide variety of potential applications, several features of all-in-one CRISPR II system are customizable. Although the EF1-α hybrid promoter is utilized herein to drive the expression of Cas9 in the all-in-one CRISPR II systems, the design of all-in-one constructs allows easy swapping of the EF1-α hybrid promoter with any kind of pol II promoter. This feature allows all-in-one CRISPR systems to be easily adopted by researchers in different fields. The all-in-one systems described herein also simplify the cloning of gRNA by simply annealing oligos without PCR, and the transformation efficiency of this system achieves 99%. This allows the systems to be easily and cost effectively used by researchers without molecular cloning experience.

EXAMPLES

The following examples are offered to illustrate, but not limit, the claimed invention.

Example 1

Synthesis of a Human Codon-Optimized Polynucleotide Encoding the Cas9 Protein A wide variety of factors regulate and influence gene expression levels. Taking into consideration as many of these factors as possible, a polynucleotide was designed for the highest possible level of expression of Cas9 protein in both human and mouse cells. Parameters used in codon optimization included:

a) codon usage bias,
b) GC content,
c) CpG dinucleotide content,
d) mRNA secondary structure,
e) cryptic mRNA splicing sites,
f) premature PolyA sites,
g) internal chi sites and ribosomal bonding sites,
h) negative CpG islands,
i) RNA instability motif,
j) direct repeats, reverse repeats, and Dyad repeats,
k) restriction sites that may interfere with downstream applications (e.g., cloning),
l) efficiency of translational termination.

The native *S. pyogenes* Cas9 gene employs tandem rare codons that can reduce the efficiency of translation or even disengage the translational machinery. In this case, the codon usage bias was increased by upgrading the codon adaptation index (CAI) to 0.88 in human and in mouse. The GC content was adjusted to 49.93% and unfavorable peaks have been optimized to prolong the half-life of the mRNA. The stem-loop structures, which impact ribosomal binding and stability of mRNA, were broken. In addition, the optimization process modified those negative cis-acting sites and avoided 15 of the most common restriction enzymes, as well as a BsaI site, as listed below.

```
Splice    (GGTAAG)
Splice    (GGTGAT)
PolyA     (AATAAA)
PolyA     (ATTAAA)
Destabilizing (ATTTA)
PolyT     (TTTTTT)
PolyA     (AAAAAAA)
BamHI     (GGATCC)
BglII     (AGATCT)
EcoRI     (GAATTC)
EcoRV     (GATATC)
HindIII   (AAGCTT)
KpnI      (GGTACC)
NcoI      (CCATGG)
NdeI      (CATATG)
NotI      (GCGGCCGC)
PstI      (CTGCAG)
SmaI      (CCCGGG)
SacI      (GAGCTC)
SalI      (GTCGAC)
XbaI      (TCTAGA)
XhoI      (CTCGAG)
```

Based on these optimization criteria, a human codon-optimized polynucleotide encoding the S. pyogenes Cas9 protein was generated. See, FIG. 10 and SEQ ID NO: 1 nucleotide positions 91 through 4191. In addition, the human codon-optimized polynucleotide encoding the S. pyogenes Cas9 protein was further manipulated by the addition of an N terminal myc-tag (see FIG. 10 and SEQ ID NO: 1 at nucleotide positions 1 through 39) and by the addition of two nuclear localization signals (NLS), located in the N terminus and C terminus, respectively (see FIG. 10 and SEQ ID NO: 1 at nucleotide positions 40 through 90, and nucleotide positions 4192 through 4242). This human codon optimized polynucleotide encoding the spCas9 modified by the addition of the N-terminal myc-tag and two NLS (located at the N-terminus and C-terminus) is referred to as hspCas9.

Example 2

Construction of an All-in-One CRISPRII System

In order to achieve high efficiency cleavage of target sequences of interest by Cas9, an all-in-one CRISPRII system was constructed by cloning the human codon optimized Cas9 sequence (hspCas9; SEQ ID NO: 1) and the crRNA-tracrRNA chimeric guide transcripts (see FIG. 1B, gRNA scaffold sequence in lowercase) into a single mammalian expression construct. The single construct engineered for use in this system is depicted in the map shown in FIG. 1A.

As shown in FIG. 1A, expression of the human codon optimized polynucleotide encoding the spCas9 (hspCas9) is driven by the EF1-α hybrid promoter.

To avoid reconstituting the RNA processing machinery, the crRNA-tracrRNA chimeric transcript (referred to as chimeric gRNA) can be easily cloned at the BsaI site with 20 base pairs of crRNA target upstream of PAM (protospacer-adjacent motif). See FIG. 1B. Expression of this chimeric gRNA sequence is driven by an upstream H1 polymerase III promoter (see FIG. 1B, H1 promoter is boxed) followed by a woodchuck hepatitis virus post-transcriptional regulatory element (WPRE) sequence to increase protein stability. The H1 promoter has no constraints on the transcription initiation site, unlike the U6 promoter which requires transcription to be initiated with a G.

FIG. 1B provides the structure of the guide sequence insertion site comprising two BsaI restriction sites. In order to target a given sequence, the construct can be digested by BsaI and a pair of annealed oligonucleotides can be cloned into the all-in-one construct. The target sequence is 20 base pairs in length (FIG. 1C, lowercase) and must be flanked on the 3'end by the NGG PAM sequence (FIG. 1C). This highly flexible approach can target any genomic site in the form of $N_{20}NGG$ (SEQ ID NO: 10).

Example 3

Expression of Prokaryote-Encoded Cas9 in Human Cells

Although the all-in-one system described in EXAMPLE 2 used the engineered humanized hspCas9 polynucleotide sequence to express Cas9, the prokaryote Streptococcus pyogenes coded cas9 (referred to as spCas9) was also tested for the ability to express in mammalian cell lines.

Figure 2A:
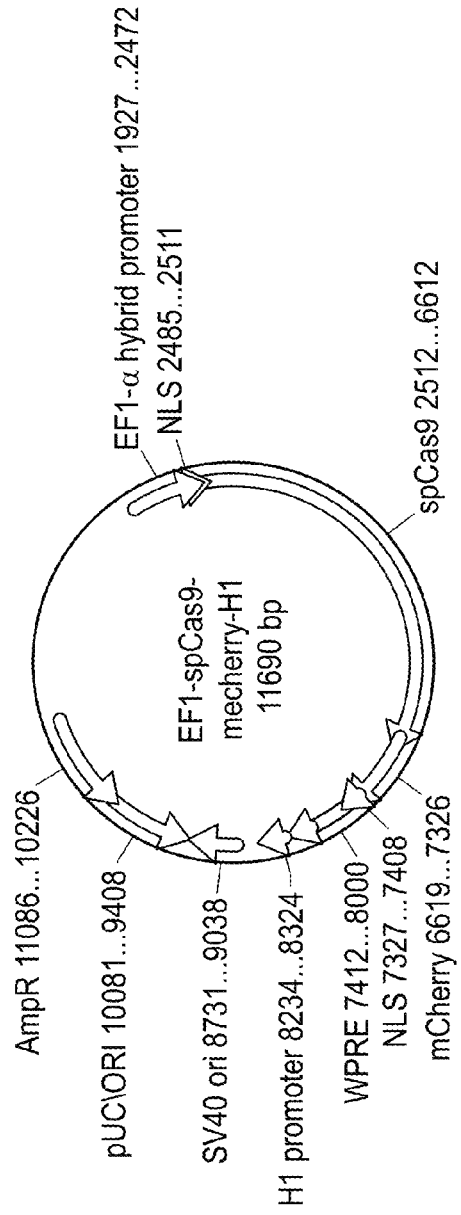
FIG. 2A provides a construct map of an expression vector containing the prokaryote encoded spCas9.

For this purpose, an expression vector containing the prokaryote encoded spCas9 was constructed, as shown in FIG. 2A. As shown in that figure, the spCas9 was augmented with N-terminus and C-terminus NLS, and further fused at the C-terminus with mcherry (red fluorescent protein), thereby allowing the monitoring of expression of spCas9 as well as cellular localization of the protein. Expression of the prokaryote encoded spCas9 was driven by the EF1-α hybrid promoter.

Figure 2B:
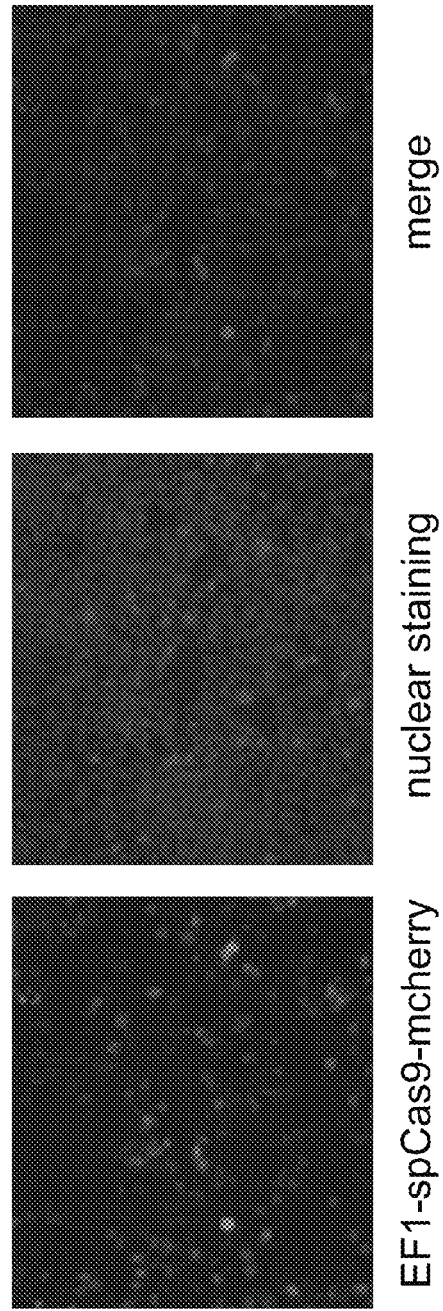
FIG. 2B provides images of human 293T cells containing the expression construct EF1-spCas9-mcherry.

Expression of this construct, termed EF1-spCas9-mcherry, in human 293T cells revealed that prokaryote encoded SpCas9 specifically express well in the nucleus of the human cells (FIG. 2B).

Example 4

Comparison of Homologous Recombination Efficiencies of CRISPRII and TALEN Genomic Targeting Systems Using a GFP Reporter To test the efficiency of stimulating genomic homologous recombination (HR) and target-sequence cleavage with the all-in-one CRISPRII system (using either hspCas9 or prokaryote spCas9 sequence), a chimeric gRNA that targets the adeno-associated virus integration site 1 (AAVS1) fragment was cloned into the all-in-one system vector, and compared its activity to that of a TAL effector nuclease heterodimer (TALEN) targeting the same region (that system termed pZT-AAVS1-TALEN).

The pZT-AAVS1-TALEN system is the most efficient TALEN pair targeting the AAVS1 fragment, as reported by others. That TALEN system shows a 25% target cleavage rate and a 8.1% HR rate in 293T cells.

Figure 3D:
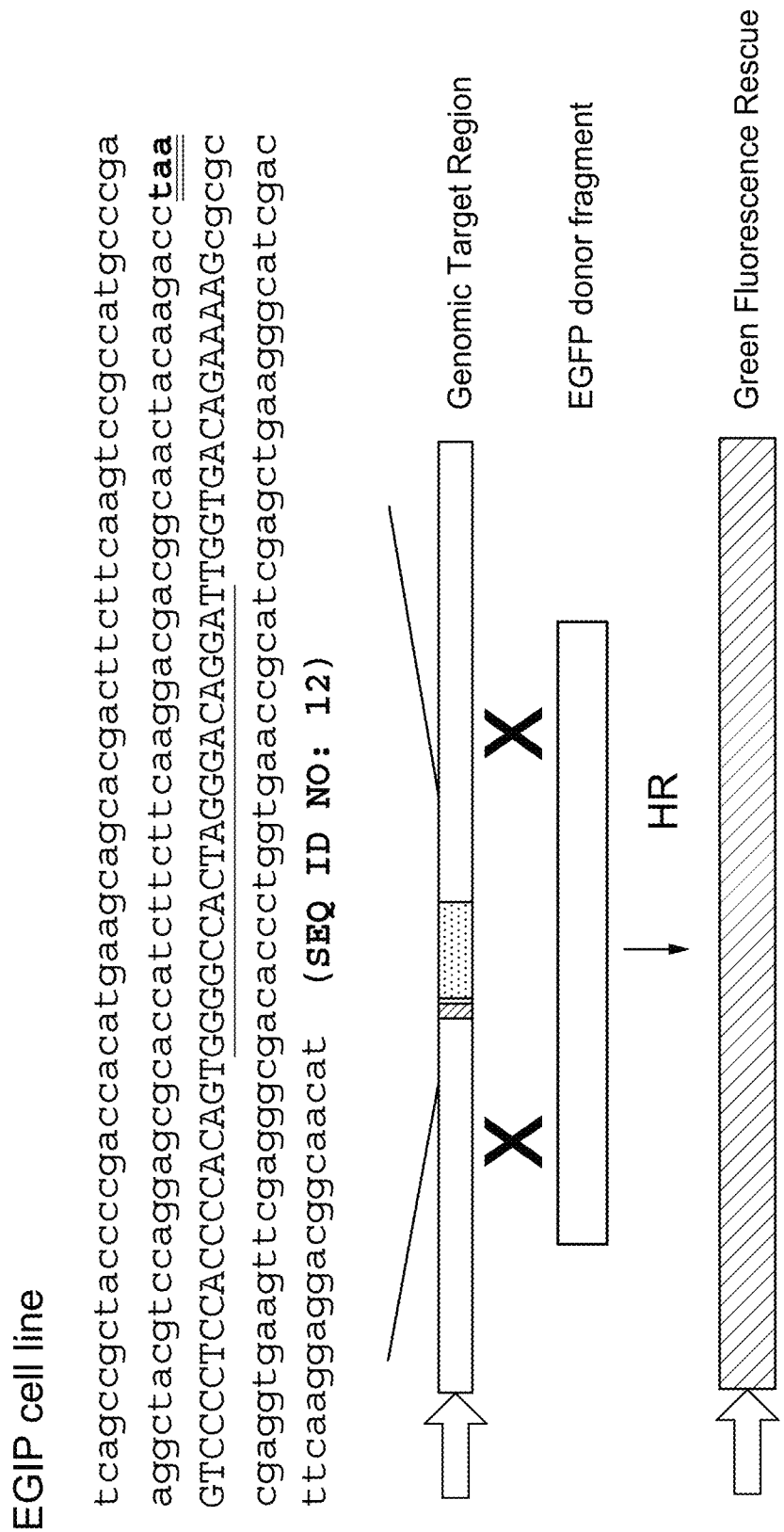
FIG. 3D provides a schematic of the synthetic nucleotide sequences and homologous recombination event in the EGIP reporter cell line.

To conduct the comparison studies, a reporter cell line termed EGIP (enhanced green fluorescent inhibited protein) was genomically engineered, as shown in FIG. 3D. This cell line contains an EGFP sequence (lowercase) bearing a stop codon (taa, double underlined) in the middle of that EGFP sequence). That stop codon is followed by a 53 base pair genomic fragment from the AAVS1 locus (uppercase nucleotides in FIG. 3D). As a result, this cell line does not express GFP. In the presence of an EGFP donor sequence, the GFP signal can hypothetically be restored by homologous recombination (HR), as illustrated in FIG. 3D. The reappearance of GFP positive signal is a marker for the cleavage and homologous recombination event in the cells. Thus, when AAVS sequence is targeted by either TALEN or Cas9, and in the presence of homologous EGFP sequence, the cell line will turn GFP positive.

In the comparison studies, pZT-AAVS1-TALEN was used as a positive control. Two different all-in-one CRISPR II systems targeting the AAVS1 locus were tested. The AAVS target sequence used in these systems is shown in FIG. 3C, and further, the location of that targeted sequence within the AAVS locus is underlined in FIG. 3D. The two CRISPR II systems tested were the human codon optimized all-in-one CRISPR II system (hspCas9 plus AAVS1 gRNA; construct EF1-hspCas9-H1-AAVS; FIG. 3A) and the prokaryote encoded all-in-one CRISPR II system (spCas9 with AAVS1 gRNA; construct EF1-spCas9-mcherry-H1-AAVS; FIG. 3B). Each of these plasmids, including the pZT-AAVS1-TALEN system, both with or without donor fragment, were transfected into EGIP 293T cells.

FIG. 4 provides fluorescent images following transfection of the various plasmids. It was observed that following the transfection of pZT-AAVS1-TALEN, EF1-hspCas9-H1-AAVSgRNA, and EF1-spCas9-mcherry-H1-AAVSgRNA constructs alone, the cells are EGFP negative. However, in the presence of donor, certain populations of the cells turn green. Both EF1-hspCas9-H1-AAVSgRNA and EF1-spCas9-mcherry-H1-AAVSgRNA in the presence of donor fragment show comparable or slightly higher HR rate as compared with pZT-AAVS1-TALEN.

Example 5

Comparison of Homologous Recombination Efficiencies of CRISPRII and TALEN Genomic Targeting Systems Using SURVEYOR® Cleavage Activity The SURVEYOR® Mutation Detection Kit assay (Transgenomic®, Inc.) also demonstrated that EF1-hspCas9-H1-AAVSgRNA and EF1-spCas9-mcherry-H1-AAVSgRNA alone can efficiently target AAVS fragment, and shows similar cleavage activity in comparison to pZT-AAVS1-TALEN. These results are shown in FIG. 5. Cleavage activity of human codon optimized all-in-one CRISPR II AAVS1 system (EF1-hspCas9-H1-AAVS) and prokaryote encoded all-in-one CRISPR II AAVS1 system (EF1-spCas9-mcherry-H1-AAVS) is compared to the activity of the pZT-AAVS1-TALEN system. From these data, it is estimated that the homologous recombination rate in EGIP 293T cells would be more than 8%, and the cleavage activity would be more than 25%. Therefore, both the human codon optimized all-in-one CRISPR II system and the prokaryote encoded all-in-one CRISPR II system are able to achieve genomic targeting and modification in a simple and highly efficient way.

Example 6

Demonstration of Homologous Recombination Activity of a Humanized CRISPRII Genomic Targeting System Using a Luciferase Reporter To further validate the all-in-one CRISPR II system, we designed a recombination monitoring system using the luciferase gene fragments as a target for genomic engineering, where the activity of the CRISPR II components can be monitored by either tracking luciferase activity or by SURVEYOR® Mutation Detection assay (Transgenomic®, Inc.). This assay system cloned and tested two different gRNAs which target the luciferase sequence.

For this purpose, a genomically engineered cell line stably expressing luciferase was established by infecting 293 cells with pGreenFire™ virus (System Biosciences, Inc.; Catalog No. TRO1OVA-1) and sorted for GFP positive cells (as both GFP and luciferase are coexpressed under the control of CMV promoter). These cells were then transfected with constructs expressing hspCas9 and luciferase gRNA, the constructs having the configuration shown in FIG. 6A. Two gRNAs which target the luciferase sequence were designed (FIG. 6B; Luc gRNA1 and Luc gRNA2; SEQ ID NOs: 13 and 14, respectively) and then cloned into the CRISPR all-in-one system expressing hspCas9 (FIG. 6A; termed EF1-hspCas9-H1-Luc).

The assay system also incorporated a donor fragment (FIG. 6C) which contains homology sequence flanking the luciferase gene, and therefore can replace the luciferase gene sequence with a red fluorescent protein (RFP) sequence. When the luciferase sequence is targeted by Cas9, in the presence of donor containing flanking dsGFP, RFP and flanking WPRE sequence, cells will turn RFP positive by homologous recombination (HR). The cleavage activity of the CRISPR II system can be monitored by using either the SURVEYOR® Mutation Detection assay (Transgenomic®, Inc.) or a luciferase assay. The homologous recombination activity can also be monitored by measuring RFP signal, as the genomic luciferase fragment would be replaced by RFP sequence (FIG. 6C).

The luciferase stable 293 cell line was transfected with either EF1-hspCas9-H1-Luc gRNA1 or EF1-hspCas9-H1-Luc gRNA2, and with or without donor. Three days after transfection, cells transfected with either EF1-hspCas9-H1-Luc gRNA1 alone or EF1-hspCas9-H1-Luc gRNA2 alone were collected for luciferase assay and SURVEYOR® assay.

Figure 7A:
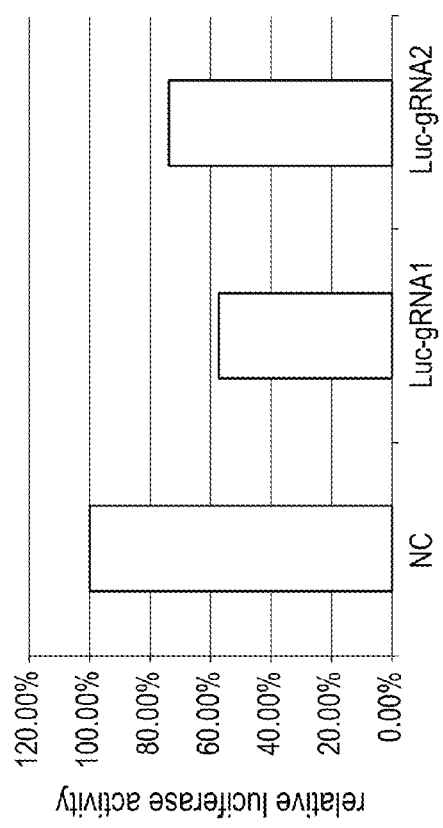
FIG. 7A provides a histogram depicting the results of a luciferase assay.

Cleavage activity of the human codon optimized all-in-one CRISPR II luciferase reporter system was assayed. It was observed that EF1-hspCas9-H1-Luc gRNA1 suppresses luciferase activity by 40% compared to untransfected negative control cells (NC). It was also observed that EF1-hspCas9-H1-Luc gRNA2 reduces luciferase activity by 25% compared to untransfected negative control cells (NC). See FIG. 7A.

Figure 7B:
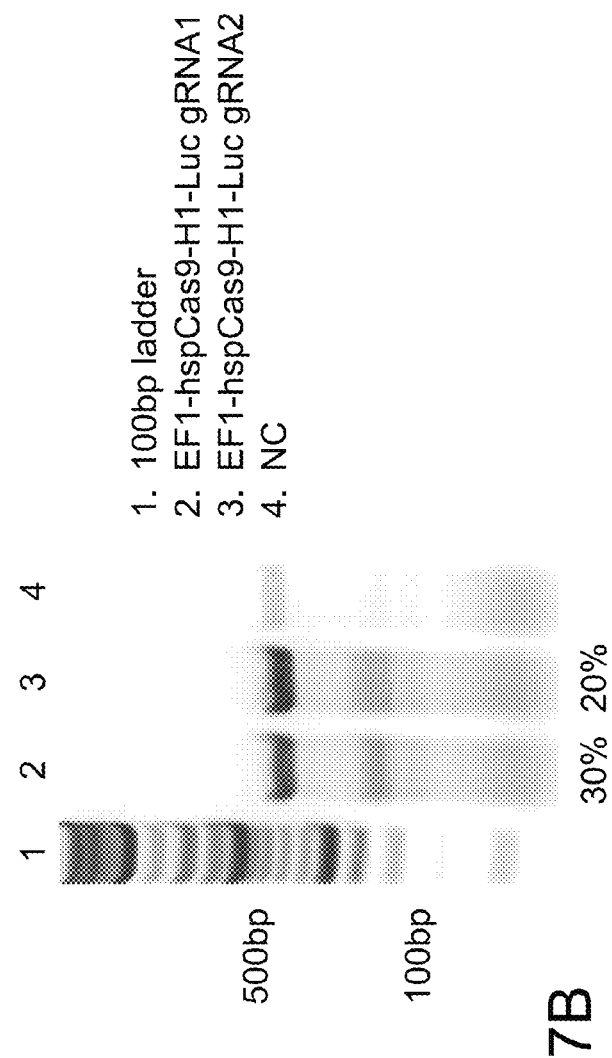
FIG. 7B provides a photograph of the results of a SUR-VEYOR® Mutation Detection Kit assay.

The SURVEYOR® assay showed results similar to the luciferase assay results. Cells transfected with EF1-hspCas9-H1-Luc gRNA1 showed 30% of the cleavage activity compared to untransfected cells, and cells transfected with the EF1-hspCas9-H1-Luc gRNA2 construct showed 22% of the cleavage activity contained in untransfected cells. See FIG. 7B.

Figure 8:
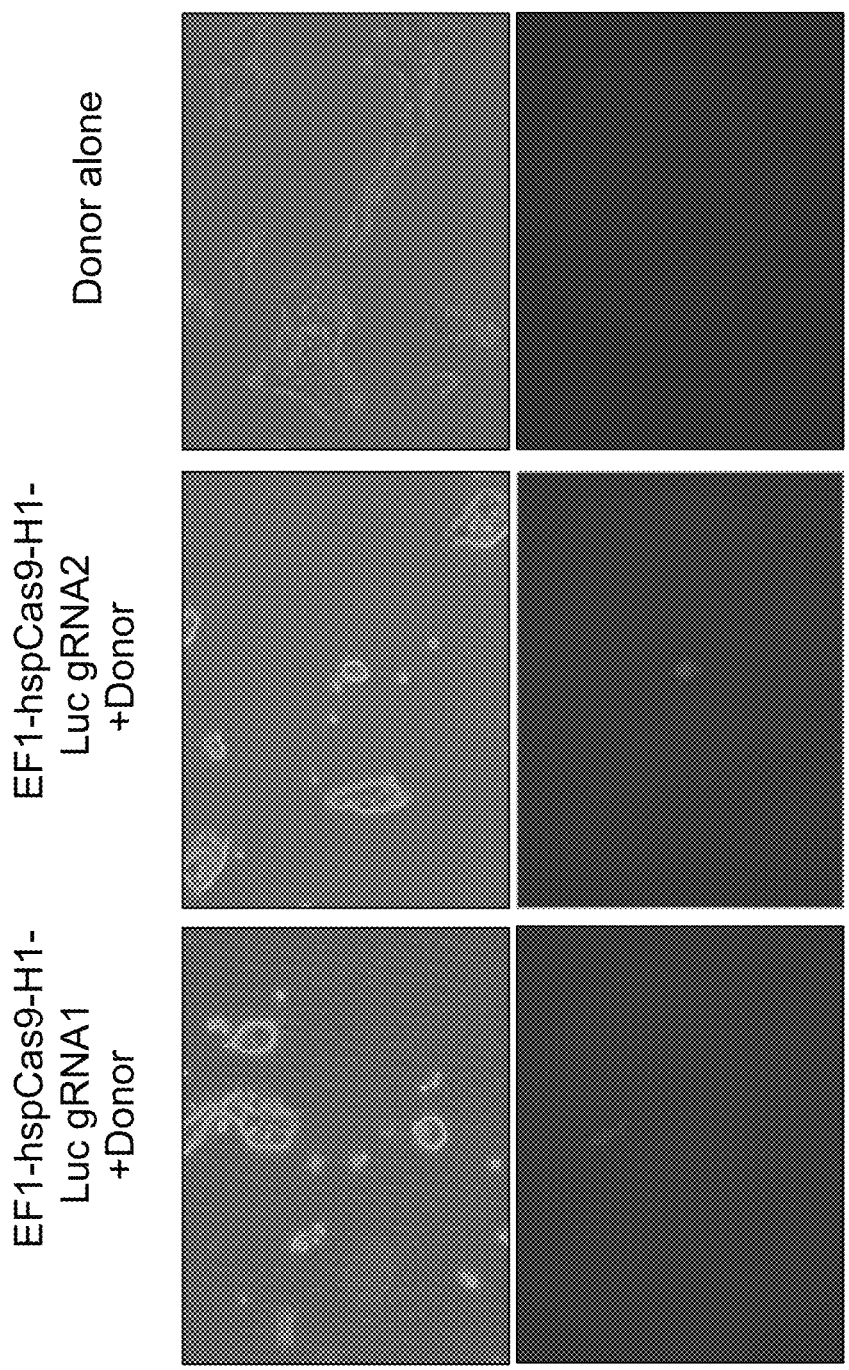
FIG. 8 provides fluorescent microscope images of cells transfected with either (i) EF1-hspCas9-H1-Luc gRNA1 and donor, (ii) cells transfected with EF1-hspCas9-H1-Luc gRNA2 and donor, or (iii) donor alone.

The efficiency of the homologous recombination event in the human codon optimized all-in-one CRISPR II luciferase system was also monitored by checking the RFP signal under a fluorescent microscope. Not surprising, RFP signal was detected in cells transfected with EF1-hspCas9-H1-Luc gRNA1 and donor, and also detected in cells transfected with EF1-hspCas9-H1-Luc gRNA2 and donor (FIG. 8).

This data further supports the notion that the engineered all-in-one CRISPR II system is a simple and robust system to achieve genomic editing.

Example 7

In Vitro Transcription Products of a Humanized CRISPRII Genomic Targeting System As described in the EXAMPLES above, the all-in-one CRISPR II system can be implemented in plasmid format. In addition, the components of the CRISPR II system can also be delivered in an mRNA format.

Figure 9:
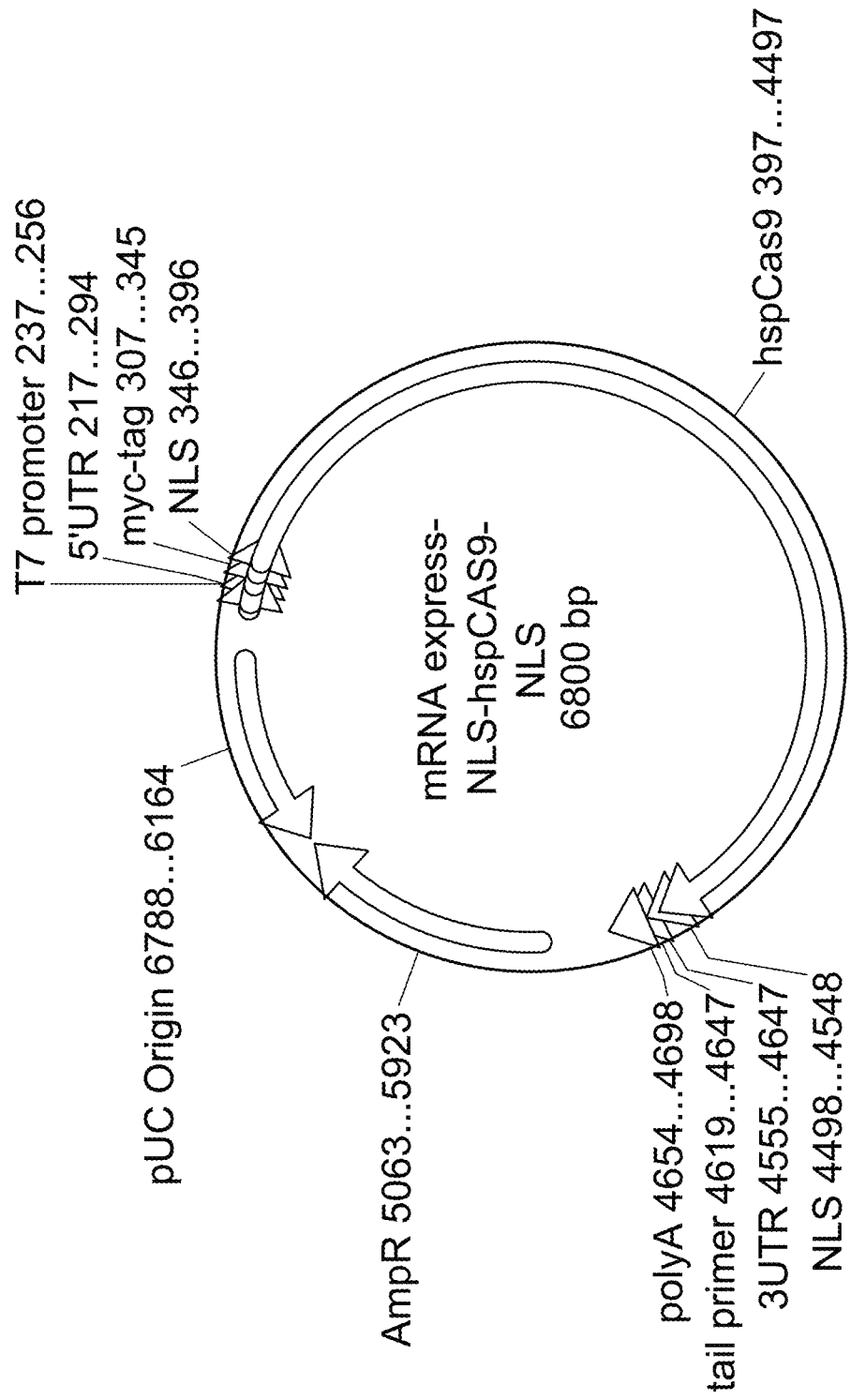
FIG. 9 provides a map of an mRNA expression vector for the expression of hspCas9 mRNA from a T7 promoter.

In order to generate in vitro transcribed CRISPR II system mRNA that can be delivered directly to cells without the need for plasmid delivery, the human codon optimized Cas9 polynucleotide was cloned into an mRNA expression vector construct, as shown in FIG. 9. This vector will express Cas9 from the T7 promoter, and will produce a Cas9 mRNA comprising two NLS sequences and a myc-tag. This will enable delivery of hspCas9 in mRNA format to achieve clean and highly efficient genomic modification.

The mRNA thus generated was tested in transfection experiments, and it was observed that the mRNA delivery is more efficient than plasmid DNA, especially in primary cells, stem cells and iPSCs. In view of this, it is contemplated that engineered hspCas9 mRNA will have broad applications such as ex vivo and in vivo gene therapy, regenerative medicine, and other applications.

Example 8 hspCas9 Sequence and Sequence Alignments

The nucleotide sequence of hspCas9 is provided in FIG. 10 and SEQ ID NO: 1. As shown in FIG. 10, the initial ATG is indicated by double underline, and the terminal TGA stop codon is shown by dashed underline. The nucleotides comprising the myc-tag sequence are nucleotide positions 1 through 39, and are shown in lowercase letters. The nucleotides comprising the N-terminal and C-terminal nuclear localization signals (NLS) are nucleotide positions 40 through 90, and positions 4192 through 4242 (including the stop codon TGA), respectively, and are indicated by single underline.

FIG. 11 provides a nucleotide sequence alignment of two sequences, where the query sequence is the hspCas9 domain containing only the Cas9 coding region, without sequences encoding the myc-tag or NLS, i.e., the query sequence is nucleotide positions 91 through 4191 of the nucleotide sequence provided in FIG. 10, and SEQ ID NO: 2. The subject sequence is a cas9 sequence of Mali et al., "RNA-Guided Human Genome Engineering via Cas9," Science Express (Jan. 3, 2013); SEQ ID NO: 3.

FIG. 12 provides a nucleotide sequence alignment of two sequences, where the query sequence is the hspCas9 domain containing the N-terminal and C-terminal NLS, and without sequences encoding the myc-tag, i.e., the query sequence is nucleotide positions 40 through 4242 of the nucleotide sequence provided in FIG. 10, and SEQ ID NO: 4. The subject sequence is a cas9 sequence of Cong et al., "Multiplex Genome Engineering Using CRISPR/Cas Systems," Science Express (Jan. 3, 2013); SEQ ID NO: 5.

While the foregoing disclosure has been described in some detail for purposes of clarity and understanding, it will be clear to one skilled in the art from a reading of this disclosure that various changes in form and detail can be made without departing from the true scope of the invention. It is to be understood that the invention is not limited to any of the specifically recited methodologies, reagents or instrumentation that are recited herein, where similar methodologies, reagents or instrumentation can be substituted and used in the construction and practice of the invention, and remain within the scope of the invention. It is also to be understood that the description and terminology used in the present disclosure is for the purpose of describing particular embodiments of the invention only, and is not intended that the invention be limited solely to the embodiments described herein.

As used in this specification and the appended claims, singular forms such as "a", "an" and "the" include plural referents unless the content clearly dictates otherwise. For example, reference to "a plasmid" includes a plurality of plasmids; reference to "a cell" also refers to cultures or populations of cells. All industry and technical terms used herein have the same meaning as commonly understood by one of ordinary skill in the art or industry to which the invention pertains, unless defined otherwise.

What is claimed is:

1. A polynucleotide comprising the nucleotide sequence of positions 91 through 4191 of SEQ ID NO: 1.

2. The polynucleotide of claim 1, wherein the polynucleotide comprises the nucleotide sequence of positions 40 through 4242 of SEQ ID NO: 1.

3. The polynucleotide of claim 1, wherein the polynucleotide comprises the nucleotide sequence of SEQ ID NO: 1.

4. The polynucleotide of claim 1, wherein the polynucleotide further comprises at least one operably linked nucleotide sequence encoding a nuclear localization signal.

5. An expression construct comprising the polynucleotide of claim 1.

6. An expression construct comprising the polynucleotide of claim 1, where the expression construct is a mammalian expression construct.

7. An mRNA expression construct comprising: (i) the polynucleotide of claim 1, and (ii) a second polynucleotide comprising a T7 promoter, wherein the T7 promoter is operably linked to the polynucleotide of claim 1.

* * * * *

SEQUENCE LISTING

```
<160> NUMBER OF SEQ ID NOS: 14

<210> SEQ ID NO 1
<211> LENGTH: 4242
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggctagta tgcagaaact gattagtgaa gaggacctga tggctcccaa gaagaagcga        60
aaggtgggca tccacggcgt gcccgctgcc gacaaaaagt atagtatcgg actggatatt       120
ggcactaaca gcgtgggatg ggccgtcatc accgacgagt acaaagtgcc aagcaagaag       180
ttcaaggtcc tgggaaacac cgatagacac agtatcaaga aaatctgat tggagccctg       240
```

```
ctgttcgact cagggggagac agctgaagca actaggctga aaagaacagc taggagacgg    300
tatactcgcc gaaagaatcg gatctgctac ctccaggaga ttttctccaa cgaaatggcc    360
aaggtggacg atagtttctt tcatcgcctg gaggaatcat tcctggtcga ggaagataag    420
aaacacgaga ggcatcccat ctttggcaac attgtggacg aggtcgctta tcacgaaaag    480
taccctacaa tctatcatct gcggaagaaa ctggtggaca gcactgataa ggcagacctg    540
cgcctgatct atctggccct ggctcacatg attaagttca gggggcattt tctgatcgag    600
ggcgatctga acccagacaa ttccgatgtg gacaagctgt tcatccagct ggtccagaca    660
tacaatcagc tgtttgagga aaacccccatt aatgcatctg gggtggacgc aaaagccatc    720
ctgagtgcca gactgtctaa gagtaggaga ctggagaacc tgatcgctca gctgccaggc    780
gaaaagaaaa acggcctgtt tggaaatctg attgcactgt cactgggact gacccccaac    840
ttcaagagca atttttgatct ggccgaggac gctaagctcc agctgagcaa ggacacctac    900
gacgatgacc tggataaccct gctggctcag atcggcgatc agtacgcaga cctgttcctg    960
gccgctaaga atctgtctga cgccatcctg ctgagtgata ttctgagagt gaacaccgag   1020
attacaaaag ccccccctgtc agctagcatg atcaagagat atgacgagca ccatcaggat   1080 ctgacccctgc tgaaggctct ggtgcggcag cagctgcctg agaagtacaa agaaatcttc   1140
tttgatcaga gcaagaatgg gtacgccggc tatattgacg gcggagcttc ccaggaggag   1200
ttctacaagt ttatcaaacc tattctggag aagatggacg gcactgagga actgctggtg   1260
aaactgaatc gggaagacct gctgcggaag cagcgcacct tcgataacgg cagcatccct   1320
caccagattc atctgggaga gctgcacgca atcctgcggc gccaggaaga cttctaccca   1380
tttctgaagg ataaccggga gaagatcgaa aaaattctga ctttccgcat cccctactat   1440
gtggggcctc tggcaagagg caattcccgg tttgcctgga tgacccgcaa gtctgaggaa   1500
acaatcactc cctggaactt cgaggaagtg gtcgataagg gcgcttccgc acagtctttc   1560
attgagagga tgacaaattt tgacaagaac ctgccaaatg aaaaagtgct gcccaagcac   1620
agcctgctgt acgagtattt caccgtctat aacgaactga caaaggtgaa atacgtcact   1680
gagggcatga gaaagcctgc cttcctgtcc ggagaacaga gaaagctat cgtgacctg     1740 ctgtttaaaa ccaatcggaa ggtgacagtc aagcagctga aagaggacta cttcaagaaa   1800
attgaatgtt tcgattctgt ggagatcagt ggggtcgaag acaggtttaa cgcctctctg   1860
ggcacctacc acgatctgct gaagatcatt aaggataaag acttcctgga caacgaggaa   1920
aatgaggaca tcctggagga cattgtgctg accctgacac tgtttgagga tcgggaaatg   1980
atcgaggaac gcctgaagac ctacgcccat ctgttcgatg acaaagtgat gaaacagctg   2040
aagcgaagga gatacactgg gtggggccga ctgagcagga agctgatcaa tggcattcgc   2100
gacaaacaga gtgaaagac aatcctggac tttctgaagt cagatggctt cgctaacagg   2160
aattttatgc agctgattca cgatgactct ctgactttca agaggacat ccagaaggca   2220 caggtgtccg gacagggga ctctctgcac gagcatatcc aaacctggc cgggagcct    2280 gccatcaaga aaggcatcct ccagaccgtg aaggtggtgg acgagctggt gaaagtcatg   2340
ggaagacata agccagaaaa catcgtgatt gagatggcca gggagaatca gaccacacag   2400
aaagggcaga agaactctcg ggagcgcatg aaacgcatcg aggaagaat taggaactg    2460 gggagtcaga tcctgaaaga gcacccgtg aaaacacac agctccagaa tgagaagctg   2520
tatctgtact acctccagaa tggccgcgat atgtacgtgg accaggagct ggatattaac   2580
cgactgtcag attatgacgt ggatcatatc gtcccacagt cattcctgaa agatgacagc   2640
```

| | | | |
|---|---|---|---|
| attgacaata | aggtgctgac | ccgcagcgac | aaaaaccgag gaaagagtga taatgtcccc | 2700 |
| tcagaggaag | tggtcaagaa | aatgaagaac | tactggaggc agctgctgaa tgccaaactg | 2760 |
| atcacccagc | gaaagtttga | taacctgaca | aaagctgaga gggggggcct gtccgaactg | 2820 |
| gacaaagcag | gcttcatcaa | gcgacagctg | gtggagacaa ggcagatcac aaagcacgtc | 2880 |
| gctcagatcc | tggacagcag | gatgaacacc | aagtacgatg agaatgacaa actgatccgg | 2940 |
| gaagtgaagg | tcattacact | gaagtcaaaa | ctggtgagcg actttaggaa agatttccag | 3000 |
| ttctacaagg | tcagagagat | caacaactac | caccatgctc atgacgcata cctgaacgca | 3060 |
| gtggtcggga | ctgccctgat | taagaaatac | cctaaactgg agtctgagtt cgtgtacggc | 3120 |
| gactataagg | tgtacgatgt | cagaaaaatg | atcgccaaga gcgagcagga aattggcaaa | 3180 |
| gccaccgcta | gtatttcttt | ttactccaac | atcatgaatt tctttaagac tgagatcacc | 3240 |
| ctggcaaatg | gcgaaatccg | aaagaggcca | ctgattgaga ctaacggaga gacaggggaa | 3300 |
| atcgtgtggg | acaaaggaag | agattttgct | accgtgcgga aggtcctgag tatgccccaa | 3360 |
| gtgaatattg | tcaagaaaac | agaggtgcag | actggagggt tcagtaagga atcaattctg | 3420 |
| cctaaacgca | acagcgataa | gctgatcgcc | cgaaagaaag actgggaccc caagaagtat | 3480 |
| ggcggattcg | actccccaac | cgtggcttac | tctgtcctgg tggtcgcaaa ggtggagaag | 3540 |
| ggaaaaagca | gaaactgaa | atccgtcaag | gaactgctgg ggatcacaat tatggagagg | 3600 |
| agcagcttcg | aaaagaatcc | tatcgatttt | ctggaggcca aagggtataa ggaagtgaag | 3660 |
| aaagacctga | tcatcaagct | gccaaagtac | tctctgtttg agctgaaaa cggcagaaag | 3720 |
| cggatgctgg | caagtgccgg | cgagctgcaa | aaaggaaatg aactggccct gccctcaaag | 3780 |
| tacgtgaact | tcctgtatct | ggctagccac | tacgagaagc tgaaaggctc ccctgaggat | 3840 |
| aacgaacaga | aacagctgtt | tgtggagcag | cacaagcatt atctggacga gatcattgaa | 3900 |
| cagattagcg | agttctccaa | acgcgtgatc | ctggctgacg caaatctgga taaggtcctg | 3960 |
| tctgcataca | caaacacag | ggacaagcca | atcagagagc aggccgaaaa tatcattcat | 4020 |
| ctgttcactc | tgaccaacct | gggagccccc | gcagccttca gtatttttga cactaccatc | 4080 |
| gatcgcaaac | gatacacaag | cactaaggag | gtgctggatg ctaccctgat ccaccagagc | 4140 |
| attactgggc | tgtacgagac | aaggatcgac | ctgtcccagc tggggggaga caaacgccca | 4200 |
| gccgccacca | gaaagcagg | acaggcaaag | aagaagaagt ga | 4242 |

<210> SEQ ID NO 2
<211> LENGTH: 4102
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 2

| | | | |
|---|---|---|---|
| gacaaaaagt | atagtatcgg | actggatatt | ggcactaaca gcgtgggatg gccgtcatc | 60 |
| accgacgagt | acaaagtgcc | aagcaagaag | ttcaaggtcc tgggaaacac cgatagacac | 120 |
| agtatcaaga | aaaatctgat | tggagccctg | ctgttcgact caggggagac agctgaagca | 180 |
| actaggctga | aagaacagc | taggagacgg | tatactcgcc gaaagaatcg gatctgctac | 240 |
| ctccaggaga | tttttctccaa | cgaaatggcc | aaggtggacg atagtttctt tcatcgcctg | 300 |
| gaggaatcat | tcctggtcga | ggaagataag | aaacacgaga ggcatcccat ctttggcaac | 360 |
| attgtggacg | aggtcgctta | tcacgaaaag | taccctacaa tctatcatct gcggaagaaa | 420 |

```
ctggtggaca gcactgataa ggcagacctg cgcctgatct atctggccct ggctcacatg      480
attaagttca gggggcattt tctgatcgag ggcgatctga acccagacaa ttccgatgtg      540
gacaagctgt tcatccagct ggtccagaca tacaatcagc tgtttgagga aaaccccatt      600
aatgcatctg gggtggacgc aaaagccatc ctgagtgcca gactgtctaa gagtaggaga      660
ctggagaacc tgatcgctca gctgccaggc gaaagaaaa acggcctgtt tggaaatctg       720
attgcactgt cactgggact gaccccccaac ttcaagagca ttttgatct ggccgaggac       780 gctaagctcc agctgagcaa ggacacctac gacgatgacc tggataacct gctggctcag      840
atcggcgatc agtacgcaga cctgttcctg gccgctaaga tctgtctga cgccatcctg       900 ctgagtgata ttctgagagt gaacaccgag attacaaaag ccccctgtc agctagcatg       960 atcaagagat atgacgagca ccatcaggat ctgaccctgc tgaaggctct ggtgcggcag     1020
cagctgcctg agaagtacaa agaaatcttc tttgatcaga gcaagaatgg gtacgccggc     1080
tatattgacg gcggagcttc ccaggaggag ttctacaagt ttatcaaacc tattctggag     1140
aagatggacg gcactgagga actgctggtg aaactgaatc gggaagacct gctgcggaag     1200
cagcgcacct tcgataacgg cagcatccct caccagattc atctgggaga gctgcacgca     1260
atcctgcggc gccaggaaga cttctaccca tttctgaagg ataaccggga agatcgaa       1320 aaaattctga ctttccgcat cccctactat gtggggcctc tggcaagagg caattcccgg     1380
tttgcctgga tgacccgcaa gtctgaggaa acaatcactc cctggaactt cgaggaagtg     1440
gtcgataagg gcgcttccgc acagtctttc attgagagga tgacaaattt tgacaagaac     1500
ctgccaaatg aaaaagtgct gcccaagcac agcctgctgt acgagtattt caccgtctat     1560
aacgaactga caaaggtgaa atacgtcact gagggcatga gaaagcctgc cttcctgtcc     1620
ggagaacaga gaaagctat cgtggacctg ctgtttaaaa ccaatcggaa ggtgacagtc      1680
aagcagctga aggaggacta cttcaagaaa attgaatgtt tcgattctgt ggagatcagt     1740
ggggtcgaag acaggtttaa cgcctctctg ggcacctacc acgatctgct gaagatcatt     1800
aaggataaag acttcctgga caacgaggaa aatgaggaca tcctggagga cattgtgctg     1860
accctgacac tgtttgagga tcgggaaatg atcgaggaac gcctgaagac ctacgcccat     1920
ctgttcgatg acaaagtgat gaaacagctg aagcgaagga gatacactgg gtggggccga     1980
ctgagcagga agctgatcaa tggcattcgc gacaaacaga gtggaaagac aatcctggac     2040
tttctgaagt cagatggctt cgctaacagg aattttatgc agctgattca cgatgactct     2100
ctgactttca aagaggacat ccagaaggca caggtgtccg gacaggggga ctctctgcac     2160
gagcatatcg caaacctggc cgggagcccct gccatcaaga aaggcatcct ccagaccgtg     2220
aaggtggtgg acgagctggt gaaagtcatg ggaagacata gccagaaaaa catcgtgatt     2280
gagatggcca gggagaatca gaccacacag aaagggcaga gaactctcg ggagcgcatg      2340 aaacgcatcg aggaaggaat taaggaactg gggagtcaga tcctgaaaga gcaccccgtg     2400
gaaaacacac agctccagaa tgagaagctg tatctgtact acctccagaa tggccgcgat     2460
atgtacgtgg accaggagct ggatattaac cgactgtcag attatgacgt ggatcatatc     2520
gtcccacagt cattcctgaa agatgacagc attgacaata aggtgctgac ccgcagcgac     2580
aaaaaccgag aaagagtga taatgtcccc tcagaggaag tggtcaagaa aatgaagaac     2640
tactggaggc agctgctgaa tgccaaactg atcacccagc gaaagtttga taacctgaca     2700
aaagctgaga ggggggggcct gtccgaactg gacaaagcag gcttcatcaa gcgacagctg     2760
```

```
gtggagacaa ggcagatcac aaagcacgtc gctcagatcc tggacagcag gatgaacacc    2820
aagtacgatg agaatgacaa actgatccgg gaagtgaagg tcattacact gaagtcaaaa    2880
ctggtgagcg actttaggaa agatttccag ttctacaagg tcagagagat caacaactac    2940
caccatgctc atgacgcata cctgaacgca gtggtcggga ctgccctgat taagaaatac    3000
cctaaactgg agtctgagtt cgtgtacggc gactataagg tgtacgatgt cagaaaaatg    3060
atcgccaaga gcgagcagga aattggcaaa gccaccgcta agtatttctt ttactccaac    3120
atcatgaatt tctttaagac tgagatcacc ctggcaaatg gcgaaatccg aaagaggcca    3180
ctgattgaga ctaacggaga gacagggaa atcgtgtggg acaaaggaag agattttgct    3240
accgtgcgga aggtcctgag tatgccccaa gtgaatattg tcaagaaaac agaggtgcag    3300
actggagggt tcagtaagga atcaattctg cctaaacgca acagcgataa gctgatcgcc    3360
cgaaagaaag actgggaccc caagaagtat ggcggattcg actccccaac cgtggcttac    3420
tctgtcctgg tggtcgcaaa ggtggagaag ggaaaaagca agaaactgaa atccgtcaag    3480
gaactgctgg ggatcacaat tatggagagg agcagcttcg aaaagaatcc tatcgatttt    3540
ctggaggcca agggtataa ggaagtgaag aaagacctga tcatcaagct gccaaagtac    3600
tctctgtttg agctggaaaa cggcagaaag cggatgctgg caagtgccgg cgagctgcaa    3660
aaaggaaatg aactggccct gccctcaaag tacgtgaact tcctgtatct ggctagccac    3720
tacgagaagc tgaaaggctc ccctgaggat aacgaacaga acagctgtt tgtggagcag    3780 cacaagcatt atctggacga gatcattgaa cagattagcg agttctccaa acgcgtgatc    3840
ctggctgacg caaatctgga taaggtcctg tctgcataca caaacacag ggacaagcca    3900 atcagagagc aggccgaaaa tatcattcat ctgttcactc tgaccaacct gggagccccc    3960
gcagccttca gtattttga cactaccatc gatcgcaaac gatacacaag cactaaggag    4020
gtgctggatg ctaccctgat ccaccagagc attactgggc tgtacgagac aaggatcgac    4080
ctgtcccagc tggggggaga ca                                            4102
```

<210> SEQ ID NO 3
<211> LENGTH: 4102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gacaagaagt actccattgg gctcgatatc ggcacaaaca gcgtcggctg ggccgtcatt     60
acggacgagt acaaggtgcc gagcaaaaaa ttcaaagttc tgggcaatac cgatcgccac    120
agcataaaga gaaccctcat ggcgccctc ctgttcgact ccggggagac ggccgaagcc    180
acgcggctca aaagaacagc acggcgcaga tataccccgca gaaagaatcg gatctgctac    240
ctgcaggaga tctttagtaa tgagatggct aaggtggatg actctttctt ccataggctg    300
gaggagtcct ttttggtgga ggaggataaa aagcacgagc gccacccaat ctttggcaat    360
atcgtggacg aggtggcgta ccatgaaaag tacccaacca tatatcatct gaggaagaag    420
cttgtagaca gtactgataa ggctgacttg cggttgatct atctcgcgct ggcgcatatg    480
atcaaatttc gggacactt cctcatcgag ggggacctga acccagacaa cagcgatgtc    540
gacaaactct ttatccaact ggttcagact tacaatcagc ttttcgaaga gaacccgatc    600
aacgcatccg gagttgacgc caaagcaatc ctgagcgcta ggctgtccaa atcccggcgg    660
```

```
ctcgaaaacc tcatcgcaca gctccctggg gagaagaaga acggcctgtt tggtaatctt    720
atcgccctgt cactcgggct gacccccaac tttaaatcta acttcgacct ggccgaagat    780
gccaagcttc aactgagcaa agacacctac gatgatgatc tcgacaatct gctggcccag    840
atcggcgacc agtacgcaga cctttttttg gcggcaaaga acctgtcaga cgccattctg    900
ctgagtgata ttctgcgagt gaacacggag atcaccaaag ctccgctgag cgctagtatg    960
atcaagcgct atgatgagca ccaccaagac ttgactttgc tgaaggccct tgtcagacag   1020
caactgcctg agaagtacaa ggaaattttc ttcgatcagt ctaaaaatgg ctacgccgga   1080
tacattgacg gcggagcaag ccaggaggaa ttttacaaat ttattaagcc catcttggaa   1140
aaaatggacg gcaccgagga gctgctggta agcttaaca gagaagatct gttgcgcaaa    1200
cagcgcactt tcgacaatgg aagcatcccc caccagattc acctgggcga actgcacgct   1260
atcctcaggc ggcaagagga tttctacccc tttttgaaag ataacaggga aaagattgag   1320
aaaatcctca catttcggat accctactat gtaggccccc tcgcccgggg aaattccaga   1380
ttcgcgtgga tgactcgcaa atcagaagag accatcactc cctggaactt cgaggaagtc   1440
gtggataagg gggcctctgc ccagtccttc atcgaaagga tgactaactt tgataaaaat   1500
ctgcctaacg aaaaggtgct tcctaaacac tctctgctgt acgagtactt cacagtttat   1560
aacgagctca ccaaggtcaa atacgtcaca gagggatga gaaagccagc attcctgtct    1620
ggagagcaga agaaagctat cgtggacctc ctcttcaaga cgaaccggaa agttaccgtg   1680
aaacagctca agaagactat tttcaaaaag attgaatgtt tcgactctgt tgaaatcagc   1740
ggagtggagg atcgcttcaa cgcatccctg gaacgtatc acgatctcct gaaaatcatt    1800
aaagacaagg acttcctgga caatgaggag aacgaggaca ttcttgagga cattgtcctc   1860
acccttacgt tgtttgaaga tagggagatg attgaagaac gcttgaaaac ttacgctcat   1920
ctcttcgacg acaaagtcat gaaacagctc aagaggcgcc gatatacagg atgggggcgg   1980
ctgtcaagaa aactgatcaa tgggatccga gacaagcaga gtggaaagac aatcctggat   2040
tttcttaagt ccgatggatt tgccaaccgg aacttcatgc agttgatcca tgatgactct   2100
ctcaccttta aggaggacat ccagaaagca caagtttctg ccaggggga cagtcttcac    2160
gagcacatcg ctaatcttgc aggtagccca gctatcaaaa agggaatact gcagaccgtt   2220
aaggtcgtgg atgaactcgt caaagtaatg gaaggcata agcccgagaa tatcgttatc    2280
gagatggccc gagagaacca aactacccag aagggacaga agaacagtag ggaaaggatg   2340
aagaggattg aagagggtat aaaagaactg gggtcccaaa tccttaagga cacccagtt    2400
gaaaacaccc agcttcagaa tgagaagctc tacctgtact acctgcagaa cggcagggac   2460
atgtacgtgg atcaggaact ggacatcaat cggctctccg actacgacgt ggatcatatc   2520
gtgcccagt cttttctcaa agatgattct attgataata aagtgttgac aagatccgat    2580
aaaaatagag ggaagagtga taacgtcccc tcagaagaag ttgtcaagaa aatgaaaaat   2640
tattggcggc agctgctgaa cgccaaactg atcacacaac ggaagttcga taatctgact   2700
aaggctgaac gaggtggcct gtctgagttg gataaagccg gcttcatcaa aaggcagctt   2760
gttgagacac gccagatcac caagcacgtg gcccaaattc tcgattcacg catgaacacc   2820
aagtacgatg aaaatgacaa actgattcga gaggtgaaag ttattactct gaagtctaag   2880
ctggtctcag atttcagaaa ggactttcag ttttataagg tgagagagat caacaattac   2940
caccatgcgc atgatgccta cctgaatgca gtggtaggca ctgcacttat caaaaaatat   3000
cccaagcttg aatctgaatt tgtttacgga gactataaag tgtacgatgt taggaaaatg   3060
```

```
atcgcaaagt ctgagcagga aataggcaag gccaccgcta agtacttctt ttacagcaat    3120
attatgaatt ttttcaagac cgagattaca ctggccaatg agagattcg gaagcgacca     3180 cttatcgaaa caaacggaga aacaggagaa atcgtgtggg acaagggtag ggatttcgcg    3240
acagtccgga aggtcctgtc catgccgcag gtgaacatcg ttaaaaagac cgaagtacag    3300
accggaggct tctccaagga aagtatcctc ccgaaaagga acagcgacaa gctgatcgca    3360
cgcaaaaaag attgggaccc caagaaatac ggcggattcg attctcctac agtcgcttac    3420
agtgtactgg ttgtggccaa agtggagaaa gggaagtcta aaaaactcaa aagcgtcaag    3480
gaactgctgg gcatcacaat catggagcga tcaagcttcg aaaaaaaccc catcgacttt    3540
ctcgaggcga aaggatataa agaggtcaaa aaagacctca tcattaagct tcccaagtac    3600
tctctctttg agcttgaaaa cggccggaaa cgaatgctcg ctagtgcggg cgagctgcag    3660
aaaggtaacg agctggcact gccctctaaa tacgttaatt tcttgtatct ggccagccac    3720
tatgaaaagc tcaaagggtc tcccgaagat aatgagcaga agcagctgtt cgtggaacaa    3780
cacaaacact accttgatga gatcatcgag caaataagcg aattctccaa aagagtgatc    3840
ctcgccgacg ctaacctcga taaggtgctt tctgcttaca ataagcacag ggataagccc    3900
atcagggagc aggcagaaaa cattatccac ttgtttactc tgaccaactt gggcgcgcct    3960
gcagccttca gtacttcga caccaccata gacagaaagc ggtacacctc tacaaaggag    4020
gtcctggacg ccacactgat tcatcagtca attacggggc tctatgaaac aagaatcgac    4080
ctctctcagc tcggtggaga ca                                             4102

<210> SEQ ID NO 4
<211> LENGTH: 4203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atggctccca agaagaagcg aaaggtgggc atccacggcg tgcccgctgc cgacaaaaag      60
tatagtatcg gactggatat tggcactaac agcgtgggat gggccgtcat caccgacgag     120
tacaaagtgc caagcaagaa gttcaaggtc ctgggaaaca ccgatagaca cagtatcaag     180
aaaaatctga ttggagccct gctgttcgac tcaggggaga cagctgaagc aactaggctg     240
aaaagaacag ctaggagacg gtatactcgc cgaaagaatc ggatctgcta cctccaggag     300
attttctcca cgaaatggc caaggtggac gatagtttct tcatcgcct ggaggaatca      360 ttcctggtcg aggaagataa gaaacacgag aggcatccca tctttggcaa cattgtggac     420
gaggtcgctt atcacgaaaa gtaccctaca atctatcatc tgcggaagaa actggtggac     480
agcactgata aggcagacct gcgcctgatc tatctggccc tggctcacat gattaagttc     540 aggggggcatt ttctgatcga gggcgatctg aacccagaca attccgatgt ggacaagctg    600
ttcatccagc tggtccagac atacaatcag ctgtttgagg aaaaccccat taatgcatct     660
ggggtggacg caaaagccat cctgagtgcc agactgtcta agtaggag actgagaac        720 ctgatcgctc agctgccagg cgaaaagaaa acggcctgt ttggaaatct gattgcactg      780
tcactgggac tgacccccaa cttcaagagc aattttgatc tggccgagga cgctaagctc     840
cagctgagca aggacaccta cgacgatgac ctggataacc tgctggctca gatcggcgat     900
cagtacgcag acctgttcct ggccgctaag aatctgtctg acgccatcct gctgagtgat     960
```

```
attctgagag tgaacaccga gattacaaaa gcccccctgt cagctagcat gatcaagaga    1020
tatgacgagc accatcagga tctgaccctg ctgaaggctc tggtgcggca gcagctgcct    1080
gagaagtaca agaaatctt  ctttgatcag agcaagaatg gtacgccgg  ctatattgac    1140 ggcggagctt cccaggagga gttctacaag tttatcaaac ctattctgga gaagatggac    1200
ggcactgagg aactgctggt gaaactgaat cgggaagacc tgctgcggaa gcagcgcacc    1260
ttcgataacg gcagcatccc tcaccagatt catctgggag agctgcacgc aatcctgcgg    1320
cgccaggaag acttctaccc atttctgaag gataaccggg agaagatcga aaaaattctg    1380
actttccgca tcccctacta tgtggggcct ctggcaagag gcaattcccg gtttgcctgg    1440
atgacccgca agtctgagga aacaatcact ccctggaact tcgaggaagt ggtcgataag    1500
ggcgcttccg cacagtcttt cattgagagg atgacaaatt tgacaagaa  cctgccaaat    1560 gaaaaagtgc tgcccaagca cagcctgctg tacgagtatt tcaccgtcta taacgaactg    1620
acaaaggtga atacgtcac  tgagggcatg agaaagcctg ccttcctgtc cggagaacag    1680
aagaaagcta tcgtggacct gctgtttaaa accaatcgga aggtgacagt caagcagctg    1740
aaagaggact acttcaagaa aattgaatgt ttcgattctg tggagatcag tggggtcgaa    1800
gacaggttta acgcctctct gggcacctac cacgatctgc tgaagatcat taaggataaa    1860
gacttcctgg acaacgagga aaatgaggac atcctggagg acattgtgct gacccctgaca    1920 ctgtttgagg atcgggaaat gatcgaggaa cgcctgaaga cctacgccca tctgttcgat    1980
gacaaagtga tgaaacagct gaagcgaagg agatacactg ggtggggccg actgagcagg    2040
aagctgatca atggcattcg cgacaaacag agtggaaaga caatcctgga cttctgaag   2100 tcagatggct tcgctaacag gaatttttatg cagctgattc acgatgactc tctgactttc    2160
aaagaggaca tccagaaggc acaggtgtcc ggacaggggg actctctgca cgagcatatc    2220
gcaaacctgg ccgggagccc tgccatcaag aaaggcatcc tccagaccgt gaaggtggtg    2280
gacgagctgg tgaaagtcat gggaagacat aagccagaaa acatcgtgat tgagatggcc    2340
agggagaatc agaccacaca gaaagggcag aagaactctc gggagcgcat gaaacgcatc    2400
gaggaaggaa ttaaggaact ggggagtcag atcctgaaag agcaccccgt ggaaaacaca    2460
cagctccaga tgagaagct  gtatctgtac tacctccaga atggccgcga tatgtacgtg    2520
gaccaggagc tggatattaa ccgactgtca gattatgacg tggatcatat cgtcccacag    2580
tcattcctga agatgacag  cattgacaat aaggtgctga cccgcagcga caaaaaccga    2640
ggaaagagtg ataatgtccc ctcagaggaa gtggtcaaga aaatgaagaa ctactggagg    2700
cagctgctga atgccaaact gatcacccag cgaaagtttg ataacctgac aaaagctgag    2760
agggggggcc tgtccgaact ggacaaagca ggcttcatca agcgacagct ggtggagaca    2820
aggcagatca caaagcacgt cgctcagatc ctggacagca ggatgaacac caagtacgat    2880
gagaatgaca aactgatccg ggaagtgaag gtcattacac tgaagtcaaa actggtgagc    2940
gactttagga agatttccag gttctacaag gtcagagaga tcaacaacta ccaccatgct    3000
catgacgcat acctgaacgc agtggtcggg actgccctga ttaagaaata ccctaaactg    3060
gagtctgagt tcgtgtacgg cgactataag gtgtacgatg tcagaaaaat gatcgccaag    3120
agcgagcagg aaattggcaa agccaccgct aagtatttct tttactccaa catcatgaat    3180
ttctttaaga ctgagatcac cctggcaaat ggcgaaatcc gaaagaggcc actgattgag    3240
actaacggag agacagggga aatcgtgtgg gacaaaggaa gagatttttgc taccgtgcgg    3300
```

```
aaggtcctga gtatgcccca agtgaatatt gtcaagaaaa cagaggtgca gactggaggg   3360
ttcagtaagg aatcaattct gcctaaacgc aacagcgata agctgatcgc ccgaaagaaa   3420
gactgggacc ccaagaagta tggcggattc gactccccaa ccgtggctta ctctgtcctg   3480
gtggtcgcaa aggtggagaa gggaaaaagc aagaaactga atccgtcaa ggaactgctg    3540 gggatcacaa ttatggagag gagcagcttc gaaaagaatc ctatcgattt tctggaggcc   3600
aaagggtata aggaagtgaa gaaagacctg atcatcaagc tgccaaagta ctctctgttt   3660
gagctggaaa acggcagaaa gcggatgctg gcaagtgccg gcgagctgca aaaggaaat    3720 gaactggccc tgccctcaaa gtacgtgaac ttcctgtatc tggctagcca ctacgagaag   3780
ctgaaaggct cccctgagga taacgaacag aaacagctgt tgtggagca gcacaagcat    3840 tatctggacg agatcattga acagattagc gagttctcca acgcgtgat cctggctgac    3900 gcaaatctgg ataaggtcct gtctgcatac aacaaacaca gggacaagcc aatcagagag   3960
caggccgaaa atatcattca tctgttcact ctgaccaacc tgggagcccc cgcagccttc   4020
aagtattttg acactaccat cgatcgcaaa cgatacacaa gcactaagga ggtgctggat   4080
gctaccctga tccaccagag cattactggg ctgtacgaga caaggatcga cctgtcccag   4140
ctgggggagg acaaacgccc agccgccacc aagaaagcag acaggcaaa gaagaagaag    4200 tga                                                                 4203
```

<210> SEQ ID NO 5
<211> LENGTH: 4203
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
atggccccaa agaagaagcg gaaggtcggt atccacggag tcccagcagc cgacaagaag     60
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact cctgatcga gggcgacctg aaccccgaca acagcgacgt ggacaagctg    600
ttcatccagc tggtgcagac ctacaaccag ctgttcgagg aaaaccccat caacgccagc    660
ggcgtggacg ccaaggccat cctgtctgcc agactgagca gagcagacg gctggaaaat    720 ctgatcgccc agctgcccgg cgagaagaag aatggcctgt tcggcaacct gattgccctg    780
agcctgggcc tgacccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gcccccctga gcgcctctat gatcaagaga   1020
tacgacgagc accaccagga cctgaccctg ctgaaagctc tcgtgcggca gcagctgcct   1080
```

```
gagaagtaca aagagatttt cttcgaccag agcaagaacg gctacgccgg ctacattgac    1140
ggcggagcca gccaggaaga gttctacaag ttcatcaagc ccatcctgga aaagatggac    1200
ggcaccgagg aactgctcgt gaagctgaac agagaggacc tgctgcggaa gcagcggacc    1260
ttcgacaacg gcagcatccc ccaccagatc cacctgggag agctgcacgc cattctgcgg    1320
cggcaggaag attttttaccc cattcctgaag gacaaccggg aaaagatcga agatcctg    1380 accttccgca tcccctacta cgtgggccct ctggccaggg aaacagcag attcgcctgg    1440 atgaccagaa agagcgagga aaccatcacc ccctggaact tcgaggaagt ggtggacaag    1500
ggcgcttccg cccagagctt catcgagcgg atgaccaact tcgataagaa cctgcccaac    1560
gagaaggtgc tgcccaagca cagcctgctg tacgagtact tcaccgtgta taacgagctg    1620
accaaagtga atacgtgac cgagggaatg agaaagcccg ccttcctgag cggcgagcag    1680
aaaaaggcca tcgtggacct gctgttcaag accaaccgga agtgaccgt gaagcagctg    1740 aaagaggact acttcaagaa aatcgagtgc ttcgactccg tggaaatctc cggcgtggaa    1800
gatcggttca acgcctccct gggcacatac cacgatctgc tgaaaattat caaggacaag    1860
gacttcctgg acaatgagga aaacgaggac attctggaag atatcgtgct gaccctgaca    1920
ctgtttgagg acagagagat gatcgaggaa cggctgaaaa cctatgccca cctgttcgac    1980
gacaaagtga tgaagcagct gaagcggcgg agatacaccg gctggggcag gctgagccgg    2040
aagctgatca acggcatccg ggacaagcag tccggcaaga caatcctgga tttcctgaag    2100
tccgacggct tcgccaacag aaacttcatg cagctgatcc acgacgacag cctgacttt    2160 aaagaggaca tccagaaagc ccaggtgtcc ggcagggcg atagcctgca cgagcacatt    2220
gccaatctgg ccggcagccc cgccattaag aagggcatcc tgcagacagt gaaggtggtg    2280
gacgagctcg tgaaagtgat gggccggcac aagcccgaga catcgtgat cgaaatggcc    2340 agagagaacc agaccaccca aagggacag aagaacagcc gcgagagaat gaagcggatc    2400
gaagagggca tcaaagagct gggcagccag atcctgaaag aacacccgt ggaaaacacc    2460 cagctgcaga acgagaagct gtacctgtac tacctgcaga atgggcggga tatgtacgtg    2520
gaccaggaac tggacatcaa ccggctgtcc gactacgatg tggaccatat cgtgcctcag    2580
agctttctga aggacgactc catcgacaac aaggtgctga ccagaagcga caagaaccgg    2640
ggcaagagcg acaacgtgcc ctccgaagag gtcgtgaaga agatgaagaa ctactggcgg    2700
cagctgctga acgccaagct gattacccag agaaagttcg acaatctgac caaggccgag    2760
agaggcggcc tgagcgaact ggataaggcc ggcttcatca gagacagct ggtggaaacc    2820 cggcagatca caaagcacgt ggcacagatc ctggactccc ggatgaacac taagtacgac    2880
gagaatgaca gcctgatccg ggaagtgaaa gtgatcaccc tgaagtccaa gctggtgtcc    2940
gatttccgga aggattccca gttttacaaa gtgcgcgaga tcaacaacta ccaccacgcc    3000
cacgacgcct acctgaacgc cgtcgtggga accgccctga tcaaaaagta ccctaagctg    3060
gaaagcgagt tcgtgtacgg cgactacaag gtgtacgacg tgcggaagat gatcgccaag    3120
agcgagcagg aaatcggcaa ggctaccgcc aagtacttct tctacagcaa catcatgaac    3180 ttttttcaaga ccgagattac cctggccaac ggcgagatcc ggaagcggcc tctgatcgag    3240
acaaacggcg aaaccgggga tcgtgtgg ataagggcc gggattttgc caccgtgcgg    3300
aaagtgctga gcatgcccca agtgaatatc gtgaaaaaga ccgaggtgca gacaggcggc    3360
ttcagcaaag agtctatcct gcccaagagg aacagcgata gctgatcgc cagaaagaag    3420 gactgggacc ctaagaagta cggcggcttc gacagcccca ccgtggccta ttctgtgctg    3480
```

```
gtggtggcca aagtggaaaa gggcaagtcc aagaaactga agagtgtgaa agagctgctg    3540
gggatcacca tcatggaaag aagcagcttc gagaagaatc ccatcgactt tctggaagcc    3600
aagggctaca agaagtgaa aaaggacctg atcatcaagc tgcctaagta ctccctgttc    3660
gagctggaaa acggccggaa gagaatgctg gcctctgccg gcgaactgca gaagggaaac    3720
gaactggccc tgccctccaa atatgtgaac ttcctgtacc tggccagcca ctatgagaag    3780
ctgaagggct cccccgagga taatgagcag aaacagctgt tgtggaaca gcacaagcac    3840 tacctggacg agatcatcga gcagatcagc gagttctcca agagagtgat cctggccgac    3900
gctaatctgg acaaagtgct gtccgcctac aacaagcacc gggataagcc catcagagag    3960
caggccgaga atatcatcca cctgtttacc ctgaccaatc tgggagcccc tgccgccttc    4020
aagtactttg acaccaccat cgaccggaag aggtacacca gcaccaaaga ggtgctggac    4080
gccaccctga tccaccagag catcaccggc ctgtacgaga cacggatcga cctgtctcag    4140 ctggaggcg acaagcgtcc tgctgctact aagaaagctg gtcaagctaa gaaaaagaaa    4200
tga                                                                 4203

<210> SEQ ID NO 6
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gggaatctta taagttctgt atgagaccac ttggatcctc tggtctctgt tttagagcta    60
gaaatagcaa gttaaaataa ggctagtccg ttatcaactt gaaaaagtgg caccgagtcg    120 gtgcttttttt t                                                       131

<210> SEQ ID NO 7
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aaaaaaaagc accgactcgg tgccactttt tcaagttgat aacggactag ccttatttta    60
acttgctatt tctagctcta aaacagagac cagaggatcc aagtggtctc atacagaact    120
tataagattc cc                                                       132

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(35)
<223> OTHER INFORMATION: a, c, t, g, unknown or other

<400> SEQUENCE: 8
tgtatgagac cacttnnnnn nnnnnnnnnn nnnnn                               35
```

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(27)
<223> OTHER INFORMATION: a, c, t, g, unknown or other

<400> SEQUENCE: 9
aaacnnnnnn nnnnnnnnnn nnnnnnnaag tggtctca                              38

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 10
nnnnnnnnnn nnnnnnnnnn ngg                                              23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggggccacta gggacaggat                                                  20

<210> SEQ ID NO 12
<211> LENGTH: 252
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tcagccgcta ccccgaccac atgaagcagc acgacttctt caagtccgcc atgcccgaag      60
gctacgtcca ggagcgcacc atcttcttca aggacgacgg caactacaag acctaagtcc    120
cctccacccc acagtggggc cactagggac aggattggtg acagaaaagc gcgccgaggt    180
gaagttcgag ggcgacaccc tggtgaaccg catcgagctg aagggcatcg acttcaagga    240
ggacggcaac at                                                        252

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggcatgcgag aatctgacgc                                                  20

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
catgccagag atcctatttt                                                 20
```